United States Patent [19]

Mason et al.

[11] Patent Number: 5,310,661
[45] Date of Patent: May 10, 1994

[54] NUCLEIC ACID ENCODING THE ALPHA CHAIN PRODOMAINS OF INHIBIN AND METHOD FOR SYNTHESIZING POLYPEPTIDES USING SUCH NUCLEIC ACID

[75] Inventors: Anthony J. Mason; Peter H. Seeburg, both of San Francisco, Calif.

[73] Assignee: Genentech, Inc., South San Francisco, Calif.

[21] Appl. No.: 958,414

[22] Filed: Oct. 8, 1992

Related U.S. Application Data

[60] Division of Ser. No. 744,207, Aug. 12, 1991, Pat. No. 5,215,893, which is a division of Ser. No. 215,466, Jul. 5, 1988, Pat. No. 5,089,396, which is a division of Ser. No. 906,729, Dec. 31, 1986, Pat. No. 4,798,885, which is a continuation-in-part of Ser. No. 827,710, Feb. 7, 1986, abandoned, which is a continuation-in-part of Ser. No. 783,910, Oct. 3, 1985, abandoned.

[51] Int. Cl.$^5$ .................... C12P 21/02; C12N 15/12; C12N 1/21; C12N 5/10
[52] U.S. Cl. .................... 435/69.1; 536/23.51; 536/23.5; 435/240.2; 435/252.3; 435/320.1; 435/69.4; 935/11
[58] Field of Search .................... 435/69.1, 69.4, 320.1, 435/252.3, 240.2; 536/23.5; 935/23.51, 11

[56] References Cited

U.S. PATENT DOCUMENTS

| | | | |
|---|---|---|---|
| 4,409,139 | 10/1983 | Ling et al. | 530/300 |
| 4,624,944 | 11/1986 | Li et al. | 514/12 |
| 4,624,994 | 11/1986 | Ansel | 525/455 |
| 4,737,578 | 4/1988 | Evans et al. | 530/350 |
| 5,004,690 | 4/1991 | Light et al. | 435/138 |
| 5,102,807 | 4/1992 | DeKretser et al. | 436/518 |

FOREIGN PATENT DOCUMENTS

| | | |
|---|---|---|
| 210461 | 2/1987 | European Pat. Off. |
| WO86/0078 | 1/1986 | PCT Int'l Appl. |
| 8606076 | 10/1986 | PCT Int'l Appl. |

OTHER PUBLICATIONS

Chu, M. L. et al. 1984, *Nature* vol. 310 pp. 337–340.
Okayama, H. et al 1983, Molecular and Cellular Biology vol. 3 pp. 280–289.
Lautenberger, J. A. et al. 1983, *Gene* vol. 23 pp. 75–84.
Statement of Donald Chisum before the Subcommittee on Intellectual Property and Judicial Administration, Committee on the Judiciary, U.S. House of Representatives, Nov. 21, 1991 on H.R. 1417, Aipla Bulletin, pp. 286–296.
*Chem. Abstr.*, vol. 97 (1982) 66653.
*Chem. Abstr.*, vol. 98 (1983) 28090.
*Chem. Abstr.*, vol. 98 (1983) 28054.
*Chem. Abstr.*, vol. 95 (1981) 21821.
*Chem. Abstr.*, vol. 100 (1984) 132713.
*Chem. Abstr.*, vol. 102 (1985) 56346.
*Chem. Abstr.*, vol. 100 (1984) 80010.
*Chem. Abstr.*, vol. 102 (1985) 56271.
*Chem. Abstr.*, vol. 100 (1984) 151164.
*Chem. Abstr.*, vol. 103 (1985) 65743.
*Chem. Abstr.*, vol. 103 (1985) 2346.
*Chem. Abstr.*, vol. 103 (1985) 98855.
*Chem. Abstr.*, vol. 105 (1986) 863.
*Chem. Abstr.*, vol. 106 (1987) 96422.
*Chem. Abstr.*, vol. 102 (1985) 198182.
*Chem. Abstr.*, vol. 102 (1985) 40114.
*Chem. Abstr.*, vol. 103 (1985) 98880.
*Chem. Abstr.*, vol. 105 (1986) 35841.
*Chem. Abstr.*, vol. 103 (1985) 116999.
*Chem. Abstr.*, vol. 106 (1987) 79384.
Arbatti et al., FEBS Ltrs. 181(1):57–63 (Feb. 1985).

(List continued on next page.)

*Primary Examiner*—Richard A. Schwartz
*Assistant Examiner*—Mary E. Mosher
*Attorney, Agent, or Firm*—Janet E. Hasak

[57] ABSTRACT

DNA encoding the prepro inhibin α and β chains has been isolated. This DNA is ligated into expression vectors and used to transform host cells for the preparation of inhibin or activin. Also provided are prohormone domains and other inhibin α or β chain derivatives having therapeutic or diagnostic interest. The compositions provided herein are useful in the manipulation of fertility in animals.

16 Claims, 24 Drawing Sheets

OTHER PUBLICATIONS

Sheth et al., FEBS Ltrs. 165(1):11-15 (Jan. 1984).
Johansson et al., FEBS Ltrs. 176(1):21-26 (Oct. 1984).
Seidah et al., FEBS Ltrs. 167(1):98-102 (Feb. 1984).
Krishnan et al., Andrologia 14:409-415 (1982).
Lugaro et al., Arc. Andrology 13:261-267 (1984).
Li et al., P.N.A.S. USA 82:4041-4044 (Jun. 1985).
Ying et al., Adv. Exp. Med. Biol. 147:117-134 (1982).
Lucaro et al., Cell Biol. Int. Reports 8(10): 811 (Oct. 1984).
Sairam et al., Mol. Cell. End. 22: 231-250 (1981).
Lilja et al., FEBS Ltrs. 182(1):181-184 (Mar. 1985).
Mohapatra et al., Mol. Cell. End. 41:187-196 (1985).
Beksae et al., Int. J. Andrology 7:389-397 (1984).
Manjunath et al., Biochem. J. 241:685-692 (1987).
Ramasharma et al., Ann. N.Y. Acad. Sci. pp. 307-328 (1982).
Ramasharma et al., P.N.A.S. USA 83:3484-3486 (May 1986).
Ramasharma et al., Science 223:1199-1202 (Mar. 1984).
Kohan et al., FEBS 199(2):242-248 (Apr. 1986).
Robertson et al., Biochem. & Biophys. Res. Comm. 126(1):220-226 (Jan. 1985).
Miyamoto et al., Biochem. & Biophys. Res. Comm. 129(2):396-403 (Jun. 1985).
Mason et al., Nature 318:659-663 (Dec. 1985).
Seidah et al, FEBS, 175(2):349-355 (1984).
Ling et al., Nature, 321:779-782 (1986).
Vale et al., Nature, 321:776-778 (1986).
Mayo et al., PNAS USA, 83:5849-5853 (1986).

Fig. 1B(I)

```
1   TGTGGGCAGACCCTGACAGAAGGGGCACAGGGCTGGGTGTGGGTTCACCGTTGGCAGGGCCAGGTGAGCT 1
                                                              met trp pro gln leu leu leu leu leu ala pro
                                                              ATG TGG CCT CAG CTC CTC TTG CTG TTG GCC CCA
                   20                                                                  10
        arg ser gly his gly cys gln gly pro glu leu asp arg glu leu val leu ala lys val arg ala leu gly pro
108     CGG AGT GGC CAT GGC TGC CAG GGC CCG GAG CTG GAC CGG GAG CTT GTC CTG GCC AAG GTG AGG GCT CTG GGA CCC
                                                              30                                       40
        pro ala val thr gly glu gly asp pro gly val arg arg his ala val gly gly phe met gly phe leu gly pro
198     CCG GCA GTG ACT GGG GAA GGT GGG GAT CCT GGA GTC CGA AGA CAT GCT GTG GGG GGC TTC ATG GGC TTC CTG GGA
                                               50                                       70
        pro glu glu asp val ser gln ala ile leu phe pro ala thr gly ala arg gly asp glu pro ala ala gly glu ser glu
288     CCC GAG GAG GAT GTC TCC CAG GCC ATC CTT TTC CCG GCT ACA GGT GCC CGC GGG GAC GAG CCA GCT GCT GGA GAG TCT GAG
                                80                                       90                                      100
        glu ala glu gly leu phe thr tyr val phe arg pro ser gln his thr his leu asp leu leu ala ser ala gln val thr arg
378     GAG GCT GAG GGC CTC TTC ACA TAT GTA TTC CGG CCG TCC CAG CAC ACA CAC CTG GAC CTG CTG GCA CTA TCA GCA GTG ACT
                                                110                                      120                                     130
        thr gly leu asp arg arg gln gly met ala ala ala ala ala asp asn ser gly pro leu ala ala leu ser ser arg gly trp phe his
468     ACG GGA CTG GAC AGA CAG GGG ATG GCA GCA GCC GCC GCC AAT AGC TCT GGG CCC CTG GCA GCC CTA TCA TCC AGG GGT TTC CAC
                                        140                                                        160
        val pro met ser leu gly gln ala pro arg trp ala ala leu pro leu his pro val ala ser ala leu pro leu thr his pro val leu
558     GTG CCC ATG TCA CTG GGC CAG GCG CCC CGC TGG GCT GCT CTG CCC CTG CAC CCT GTG GCC TCT GCC CTC CCT TTG ACC CAC CCA GTC CTG
                                170                                       180                                       190
```

Fig. 1B(II)

```
                      val leu leu arg cys pro leu cys ser ala arg pro glu ala thr pro phe leu val ala his thr arg ala arg pro pro
 648                  GTG CTG CTG CGC TGT CCT CTC TGC TCA GCC CGG CCC GAG GCC ACC CCC TTC CTG GTG GCC CAC ACT CGG GCC AGG CCA CCC
                                                            ■━━━━━━━━▶ α subunit
                      ser gly gly arg ala ser thr ala pro trp pro ser phe ala ala leu arg leu leu gln arg ile val his pro pro glu
 738                  AGC GGA GGG AGG GCC TCC ACC GCC CCC TGG CCC TCC TTC GCC GCG CTG CGC CTG CTG CAG AGG ATC GTG CAC CCT CCG GAG glu pro ala val his ala asp his arg ala asp ser leu asn ile ser phe gln glu leu gly trp asp arg trp ile val his pro pro
 828                  GAA CCC GCT GTG CAC GCC GAC CAC AGA GCT CAC AGC CTC AAC ATC TCC TTC CAG GAG CTG GGC TGG GAC CGG TGG ATC GTG CAC CCT CCC ser phe ile phe his tyr cys his gly gly cys gly ala gln pro cys cys ala ala leu pro thr leu pro pro asn leu arg val pro pro thr pro
 918                  AGT TTC ATC TTC CAC TAC TGT CAC GGG GGC TGC CCG GCT CAG CCC TGC TGC GCT GCT CTC CCG ACC CTG CCC CCC AAC CTG CGA GTC CCT CCT ACC CCT val gln pro leu leu val pro gly ala gln pro cys cys ala ala leu pro thr leu pro pro asn leu arg val pro pro thr pro gly thr met arg ser leu arg val arg thr thr ser
1008                  GTC CAG CCC CTG TTG GTG CCA GGG GCT CAG CCC TGC TGC GCT GCT CTC ACC CTC CCG CCT AAC CTT CGA GTC CCT CCT ACC CCT GGG ACC ATG AGG TCC CTA CGC GTT CGC ACC ACC TCG 360         364
                      asp gly gly tyr ser phe lys tyr glu thr val pro asn leu his gln cys ala cys ile OC
1098                  GAT GGA GGT TAC TCT TTC AAG TAC GAG ACG GTG CCC AAC CTT CAC CAG CAC TGT GCC TGC ATC TAA GGGTGTCCCGCTGGTGGCCGAGCTCCC 1194                  ACAGGCACCAGCCTGGAGGAAGGCAGAGTTCCCACCTCCCCCTTCCTTCCGCCTCTCCGCCTCCCCTGTCCGCCCCCTGTCCCCATGGGTAATGTGACAATAAACAGCAT

1312                  AGTGCAGATGACTCGGTGCGCAAAAAAAA
```

Fig.2B(I)

```
                                              1                                                  10                              20
                                              met pro leu leu trp leu arg gly phe leu leu ala ser cys trp ile ile val arg ser ser
  1   AAAAGGGCCGTCACCACCAACTTTGGCTGCTGCCAGG    ATG CCC TTG CTT TGG CTG AGA GGA TTT TTG TTG GCG AGT TGC TGG ATT ATA GTG AGG AGT TCC pro thr pro gly ser gly gly his ser ala ala pro asp cys pro ser cys    ala leu pro lys asp val pro asn ser gln
                            30                                                     40                                  50
 97   CCC ACC CCA GGA TCC GGG GGC CAC AGC GCA GCC CCG GAC TGC CCG TCC TGT  GCG CTG CCA AAG GAT GTA CCC AAC TCT CAG
        pro thr pro gly ser gly gly his ser ala ala pro asp cys pro ser cys  ala leu pro lys asp val pro asn ser gln pro glu met val glu ala val lys lys      met his leu asn              val gly lys val     thr gln pro  asp ile leu glu asp asp ile    arg arg ala
                                                                                                                             80
187   CCG GAG ATG GTG GAA GCC GTC AAG AAG  ATG CAC TTG AAC AAC  GTG GGG AAA GTG  ACC CAG CCG GAT ATC GAG GAC GAC ATC  AGG AGG GCG
        pro glu met val glu ala val lys lys  met his leu asn asn  val gly lys val  thr gln pro asp ile leu glu asp asp ile  arg arg ala 90                                          100                                    130
        ala leu asn glu met leu met ile  arg lys lys lys   leu his val   gly glu asn gly     val glu glu glu    leu glu asp asp leu    gly thr ala
277   GCG CTT GAA GAA CTG ATG ATC ATC   AGA AAG AAG AAA   CTT CAT GTG   GGG GAG AAC GGG    GTG GAG GAG GAG    CTG GAG GAC GAC CTG     GGC ACC GCC
        ala leu asn glu met leu met ile  arg lys lys lys   leu his val   gly glu asn gly     val glu glu glu    leu glu asp asp leu    gly thr ala glu met asn glu leu met gln leu met ala      phe ala glu ala     ser glu ile ile thr     tyr ala     arg lys thr leu arg ala       phe
                                                   120                                                                                          130
367   GAA ATG AAT GAA CTC ATG CAA CTC ATG GCA   TTC GCG GAA GCA   TCG GAG ATC ATC ACC   TAC GCC   AGG AAG ACG CTG CGC GCG    TTT
        pro gly ala asp val gln gln glu ala glu  phe ala glu ala  ser glu ile ile thr   tyr arg  arg lys thr leu arg ala      phe
```

Fig.2B(II)

Fig. 2B(III)

Fig. 2B(IV)

```
1360  GAAGACACGTTTACGGCCTCTGACCTAGGCGACCGCAAACATGAAATGAACAAAACTAAAAACAAAACTGAAACAGATGAAGGAAGACGTGGAAAATTCCGTAGCC
      TGTGGTCTTGCCGCTGGGTGGCCCGGCAGGTGCCAGGTGGAGGCCTGAGATACTTTCCTACTTCTTTATTGAGCAATCAGTCGAAACCAGAGGCGGACCCTCCGTGGACACGAAAGA

1480  AGGGCTCGGCGATGACACCGTGAAGGAGACGGACTCGGGGGAGGGAGGCAGAACGTGGGGGCGGGGGACGACCCTTCCTTCTTCCTCCAGCATCGGAGTGGGGAC
      CTTGAAAATGCACACGTAGATGCCCGAGCAGACGCCTCCTGCCACCCACACAGCAGCCTCGGGATACCGACCCAGCAATGGCAGCTTAGCTACAAACGCCTGTCAG

1600  AGCAGTTGCTCCAACGGGAATATTGTCTCTCCTCCTTTTCAGTTCCCTGTCAGTGTGAGCCTCTGAGCCTCGAAGTCAGCTTGTCTGCAGCCATGTGGGCTGGCACAACCCAAATAGCTCTAGA
      TCGGAGAGAAAGGGTGAGCAGCACCATTCCACCAGCTGGCCACTCTGAATCGCTCCTTTGAGACACCAGAAAAGCACAAGACAGAGACACCGAGAGAGAGAGAGAGAGAGA

1720  AAGCCATGAGTTTGAAAGGGCCAGTTATAGGCACTTTCCACCCAGTAACCCAGGTCGTAAGGTATGTCTGTGTGACCCTCTCTCTGTGTATATCAGCCCTACAAAGAC
      GAGACAGACAGACAGAGAGAGAGAGAGAGCGAGAGAGCGAGAGAGAGAGAGAGAGAG

1840  ACACACACACACACACACACACACACACACACAACTTCCTCTGACTTTTCTGAGACAAAGAGGTGGGTATAAACTGACTCCAGGAAAACTCGAG
1960  TGGGAAAACGTGCCCTTTGGGACAATTTAGATGGTGGAGACAAGGCAAGAAAAAGGAGGCAACGGCAAGGTCATTGTTCGTGATGGGCCTGTGCCCCTGAGGGAGGGGTGAGGAAGTCCCTA
2080  AGGGTGACCTTAGCAGAGTGACTCTAGAAGGGGCTCGACAGGGTCGAGGTTGAGGTTCGATCCGACTGGGTTAACGATCCGGCGTTGCGTGGTGCAGGTTGCAGACG
2200  TCGTGGGCAGTGGTTAACGAATCGACTAGGAACCATGAGGTTGAGCCTTACTCAGTGGGTTACCTGCCCTTACTCAGCCTGGGAACCTCCATATGCCGGCCCCAGAAATAGCAAAGAATAAAAG
2320  CGGCTCGGATCCTGGCTCTGCGTGGTCGTTGAGGGTCTGGCTAGGGCGGTGCTACAGCTCCAGTCAACCCCAGTGGGAACCTCCATATGCCGGCCCCAAGAATAGCAAAAGAATAAAAG
2440  AGAACCACCGTGGAGGCCCGTAGCCAGAGCCCGGTCCCTTTAACCCAAGTAGGGAAAGGGAATGAAGACTAAGAAGTGAATTTCTTGACAGTCGAGGTGATATTCCACCTTTCGCTTTAGCAGTA
2560  AGTGCCTCTTCCTGGGAGGCGAGACTAAGGCTTCCATTCAGTCCGTATTGCCGTAGCACCCTGCGTTGAGATGGGCATGGTGGAGGCATGTATTCAACCCTACAGTTGTTCACGTGTATCTTGTT
2680  TCTGAAGTCACGGCCGAGACTACACTATTTGAGAACCAAGACCTGTCTATTGCTCTAGCACCACCAGTTCCAGGGACCAGTCTCCACGGTCCCTCTTCCAAGCTCTCCTTGCCAGGAACAC
2800  TGCTGGTTAAACCCTACCTACACTATTTGAGAACCAAGACCTGTCTATTGCTCTAGCACCACCAGTTCCAGGGACCAGTCTCCACGGTCCCCTCTTCCAAGCTCTCCTTGCCAGGAACAC
2920  ATTCCTCTCTGCCCAGCTCACTCTGCCCACAGAGTCAGCCTGCATCATGCAGAGATTCTGTCATCACCGTTCTCATTCAGATTCTTCCATTGGCTGGCTTCTGCGCAAAGCACACGGACTGTTC
3040  CCATCTCCCCTCCGTTCCTGCCACAGAGTCAGCCTGCATCATGCAGAGATTCTGTCATCACCGTTCTCATTCAGATTCTTCCATTGGCTGGCTTCTGCGCAAAGCACACGGACTGTTC
3160  AATTCAAAGAGCTTGTAACTCCCATTTTCCACCTTATTACAATCATAAGTCAGCCTGTACCATGACACCCCCCTGGTTTCCTCGGGAGACGTAATTGGCTGGCAGGACCTTTTGATGTAGGTCAAGACTTTTTGTTAAATCTTCTCTTAGCACCA
3280  TCTCCGCTTGTAACTCCCATTTTCCACCTTATTACAATCATAAGTCAGCCTGTACCATGACACCCCCCTGGTTTCCTCGGGAGACGTAATTGGCTGGCAGGACCTTTTGATGTAGGTCAAGACTTTTTGTTAAATCTTCTCTTAGCACCA
3400  TGCCTGTTTCATGACACTTCATAGCACTTATTACAATCATAAGTCAGCCTGTACCATGACACCCCCCTGGTTTCCTCGGGAGACGTAATTGGCTGGCAGGACCTTTTGATGTAGGTCAAGACTTTTTGTTAAATCTTCTCTTAGCACCA
3520  ATTCCCAGTGTCGGGCACACAGTTGTTGCTCAATAAATTTGCTCAATAAATTTGACTTAATGAACTCAAAAAAAAAAAAA
```

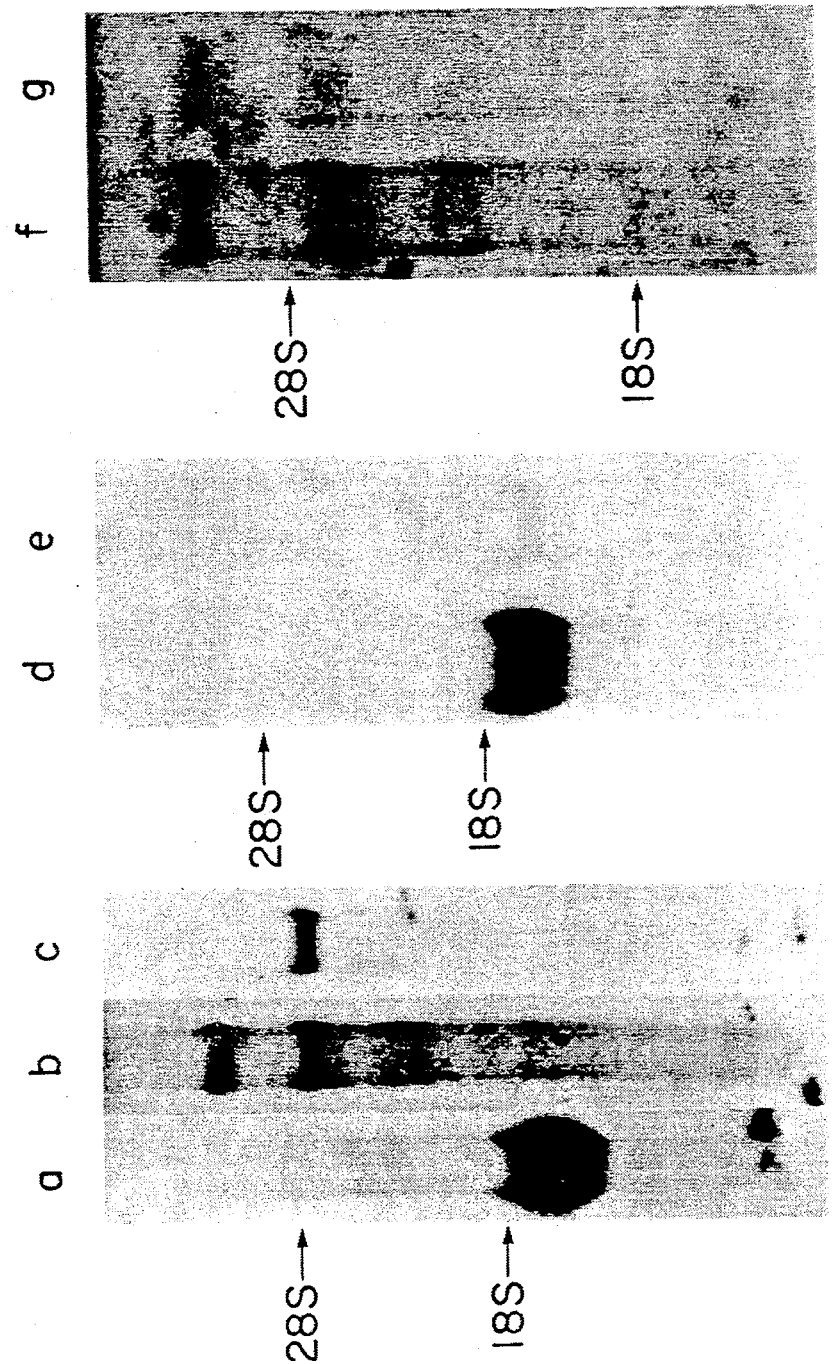

Fig. 4A.

```
p.βA-Inh:  GLE---CDGKVNI-CCKKQFFVSF-KDIGWNDWIIAPSGY   HANYCEGECPSHIAGTSGSSLSFHSTVINHYRMRGHSPFA   NLKSCCVPTKLRPMSMLYYDDGQNIIKKDIQNMIVEECGCS
           *    *      *    * **    *               *    *                  *                  *   *       *     *         *   *
h.β-TGF:   ALDTNYCFSSTEKNCCVRQLYIDFRKDLGWK-WIHEPKGY   HANFCLGPCPYIWSLDT----QYSKVLAL-YNQ--HNPGA   SAAPCCVPQALEPLPIVYYV-GRKPKVEQLSNMIVRSCKCS
                 *    *   *      *     *                 *   *               *                       *    *       *                *   *
p.βB-Inh:  GLE---CDGRTNL-CCRQQFFIDFRL-IGWSDWIIAPTGY   YGNYCEGSCPAYLAGVPGSASSFHTAVVNQYRMRGLNPG-   TVNSCCIPTKLSTMSMLYFDDEYNIVKRDVPNMIVEEGGA
           *    *      *  **     *    *              *   *   *                   *                *  *        *         **      *  *
```

Fig. 4B.

```
                 1                                                                    39
p.βA-Inh:        GLECDGK VNI- C KKQFFV SF KDIGWND WIIA P SGYHAN Y
p.α -Inh:        RPPEEPA V HAD C HRASLNI SF QELGWDR WIVH P PSFIFH Y
                                *        *         **       *         *
                 19                                                   58

40                                                   79
p.βA-Inh:         C  E  C  PSHIAGTSGSS L SFHSTVINHYRMRGHSPFANLKS
p.α -Inh:         C H GG GLPTLPNLPL S VPGAPPTPVQPLLLVPGAQ----P
                  *    *             *                      *
                 59                                                   94

80                                                   116
p.βA-Inh:         CC  VPTKLRPM S MLYY--DDG Q -NIIKKDI Q NMIVEE GG S
p.α -Inh:         CC  AALPGTMR S LRVRTTSDG GYSFKYETVP N LLTQH C A C I
                  *           *           *            *       **     *
                 95                                                   134
```

Fig.6A.

```
                    -16  Gly Val Ser Ser Gln Gly Leu Glu Leu Val Leu Ala Lys Val Arg Ala Leu Phe Leu Asp
  1 GT                   GGG GTC AGC AGC CAG GGG CTG GAG CTT GTT CTG GCC AAG GTG AGG GCC CTG TTC TTG GAT
                         -10                                  -1  +1                              30
        Ala Leu Gly Pro Pro Ala Val Thr Arg Glu Gly Asp Pro Gly Val Arg Leu Arg Pro Arg His Ala Leu
 75     GCC TTG GGG CCC CCC GCG GTG ACC AGG GAA GGT GAC CCT GGA GTC AGG CTG CGG CCC CGA AGA CAT GCC CTG
                10                              40                              50

Gly Gly Phe Thr His Arg Gly Ser Glu Pro Glu Glu Glu Asp Val Ser Gln Ala Glu Glu Ala Ile Leu Phe Pro Ala Thr
150     GGG GGC TTC ACA CAC AGG GGC TCT GAG CCC GAG GAA GAG GAT GTC TCC CAA GCC GAG GAG GCT ATC CCA GCC ACA
                                                        60                              70                              80

Asp Ala Ser Cys Glu Asp Lys Ser Ala Ala Arg Pro Ser Gln His Thr Arg Ser Arg Gln Val Thr Gly Leu Phe Arg Tyr Met
225     GAT GCC AGC TGT GAG GAC AAG TCA GCT GCC AGA CGC CAT CAG CAC ACA CGC AGC CGC CAG GTG ACT TCA GGG CTC TTC AGA TAC ATG
                                        90                              100

Phe Arg Pro Ser Gln His Thr Arg Ser Arg Gln Val Thr Gly Leu Trp Phe His Thr Gly Leu Asp Arg
300     TTC CGG CCA TCC CAG CAT ACA CGC AGC CGC CAG GTG ACT TCA GGG CTG TGG TTC CAC ACC GGG CTG GAC AGG
                                                                                    120                              130

Gln Gly Thr Ala Ala Ser Asn Ser Glu Pro Leu Leu Val Leu Ala Thr Ser Pro Gly Gly Pro Val Ala
375     CAG GGC ACA GCA GCC TCC AAT AGC TCT GAG CCC CTG CTA GCA CTG GCC ACC TCA CCG GGA GGA CCC GTG GCT
                                                                                    130

Val Pro Met Ser Leu Gly His Ala Pro Pro His Trp Ala Val Leu His Leu Ala Thr Ser Ala Leu Ser Leu Leu
450     GTG CCC ATG TCT CTT TTG GGC CAT GCT CCC CCT CAC TGG GCC GTG CTG CAC CTG GCC ACC TCT GCT CTC TCT CTG CTG
                              140                                                   150

Thr His Pro Val Leu Leu Val Leu Leu Arg Pro Leu Cys Thr Cys Ser Ala Arg Pro Glu Ala Thr Pro Phe
525     ACC CAC CCC GTC CTG CTG GTG CTG CTG CGC CCC CTC TGT ACC TGT TCA GCC CGG CCT GAG GCC ACG CCC TTC
                              160                                                   170                              180
```

Fig. 6B.

→ α subunit

```
      Leu Val Ala His Thr Arg Pro Ser Gly Gly Glu Arg Ala Arg Ser Thr Pro Leu Met Ser Trp
600   CTG GTG GCC CAC ACT CGG CCA AGT GGA GGG GAG AGA GCC CGA TCA ACT CCC CTG ATG TCC TGG
                             190                                              230
      Pro Trp Ser Pro Ser Ala Leu Arg Leu Leu Gln Arg Pro Pro Glu Glu Pro Ala Ala His Ala Asn
675   CCT TGG TCT CCC TCT GCT CTG CGC CTG CTG CAG AGG CCT CCG GAG GAA CCG GCT GCC CAT GCC AAC
      210                                      220
      Val Ala Leu Asn Ile Ser Phe Gln Glu Leu Gly Trp Glu Arg Trp Ile Val Tyr Pro Pro Ser Phe Ile Phe His
750   GTA GCA CTG AAC ATC TCC TTC CAG GAG CTG GGC TGG GAA CGG TGG ATC GTG TAC CCT CCC AGT TTC ATC TTC CAC
                 240                                              250
      Tyr Cys His Gly Gly Leu His Ile Pro Pro Asn Leu Ser Leu Pro Val Pro Gly Ala Pro Pro Thr Pro
825   TAC TGT CAT GGT GGT CTG CAC ATC CCA CCA AAC CTG TCC CTT CCA GTC CCT GGG GCT CCT CCC ACC CCA
          260                                              270                          280
      Ala Gln Pro Tyr Ser Leu Leu Pro Gly Ala Gln Pro Cys Cys Ala Ala Leu Pro Gly Thr Met Arg Pro Leu His
900   GCC CAG CCC TAC TCC TTG CTG CCA GGG GCC CAG CCC TGC TGC GCT GCT CTC CCA GGG ACC ATG AGG CCC CTA CAT
                 290                                          300                                  330
      Val Arg Thr Thr Ser Asp Gly Gly Tyr Ser Phe Lys Tyr Glu Thr Val Pro Asn Leu Leu Thr Gln His Cys Ala
975   GTC CGC ACC ACC TCG GAT GGA GGT TAC TCT TTC AAG TAT GAG ACA GTG CCC AAC CTT CTC ACG CAG CAC TGT GCT
              310                                           320
      335 Ile OC*
1050  ATC TAA  GGGTGGGGGGTCTTCCTTCTTAATCCCATGGCTGGTGGCCACGCCCCACCATCATCAGCTGGGAGGAAAGGCAGAGTTGGGAAATA

1146  GATGGCTCCCACTCCTCCCTCCTTTCACTTCTCTGCCTATGGGCTACCCTCCCACCCCACTTCTATCTCAATAAAGAACACAGTGCATATG polyA
```

Fig. 7A.

```
              -30                           +1                          20
pin.alpha     MWPQLLLLLLLAPRSGHGCQGPELDRELVLAKVRALFLDALGPPAVTGEGG
hin.alpha                      GVSSQGLELARELVLAKVRALFLDALGPPAVTREGG
                               ***                              *

40                          60
pin.alpha     DPGVRRLPRRHAVGGFMRRGSEPEEE-DVSQAILFPATGARCGDEPAAGE
hin.alpha     DPGVRRLPRRHALGGFTHRGSEPEEEEDVSQAILFPATDASCEDKSAARG
                          *    **               *   *   ****

80                         100
pin.alpha     LAREAEEGLFTYVFRPSQHTHSRQVTSAQLWFHTGLDRQGMAAANSSGPL
hin.alpha     LAQEAEEGLFRYMFRPSQHTRSRQVTSAQLWFHTGLDRQGTAASNSSEPL
                *        * *        *                  *   *  *

120                  140                         160
pin.alpha     LDLLALSSRGPVAVPMSLGQAPPRWAVLHLAASALPLLTHPVLVLLLRCP
hin.alpha     LGLLALSPGGPVAVPMSLGHAPPHWAVLHLATSALSLLTHPVLVLLLRCP
               *    * *          *   *        *   *
``` pin.alpha
hin.alpha pin.alpha
hin.alpha pin.alpha
hin.alpha pin.alpha
hin.alpha

Fig. 7B.

```
                        180                    200
pin.alpha   LCSCSARPEATPFLVAHTRARPPSSGGERARRSTAPLP-WPWSPAALRLLQ
hin.alpha   LCTCSARPEATPFLVAHTRTRPPSGGERARRST-PLMSWPWSPSALRLLQ
             *                               *     **       *

220                    240                    260
pin.alpha   RPPEEPAVHADCHRASLNISFQELGWDRWIVHPPSFIFHYCHGGCGLPTL
hin.alpha   RPPEEPAAHANCHRVALNISFQELGWERWIVYPPSFIFHYCHGGCGLHIP
                  *  *   **                *  *              ***

280                    300
pin.alpha   PNLPLSVPGAPPTPVQPLLLVPGAQPCCAALPGTMRSLRVRTTSDGGYSF
hin.alpha   PNLSLPVPGAPPTPAQPYSLLPGAQPCCAALPGTMRPLHVRTTSDGGYSF
               * *          *  * **              *  *

320                   334
pin.alpha   KYETVPNLLLTQHCACI
hin.alpha   KYETVPNLLLTQHCACI
```

Fig.8A.

```
  1 TGCTCCCTGACACAGCCACAAACCTACAGCACTGACTGCATTCAGAGAGGAACCTGCAAACAAAACTTCAGAGAAACTTTTGTTCTTGTTCCAGAGAATT

101 TGCTGAAGAGGAGGAAGGAAAAAAAAAACACCACAAAAATAAAAAATCCACACAAAAACCTGCCGTGAGGGGGAGGAAAGCAGGCCT

-28
201 TTTAAAAGGCAATCACACAACTTTTGCTGCCAGG  Met Pro Leu Leu Trp Leu Arg Gly Phe Leu Leu Ala Ser Cys Trp
                                        ATG CCC TTG CTT TGG CTT AGA GGA TTT CTG TTG GCA AGT TGC TGG
                  -10                                            -1  +1
    Ile Ile Val Arg Ser Ser Pro Thr Pro Gly Ser Glu Gly His Gly Ser Ala Pro Asp Cys Pro Ser Ala Leu
282 ATT ATA GTG AGG AGT TCC CCC ACC CCA GGA TCC GAG CAC GGG AGC GCG GCC GAC CCC TGT CCG TCC GCG CTG
                                                                                10
    Ala Ala Leu Pro Lys Asp Val Pro Asn Ser Gln Pro Glu Met Val Glu Ala Leu Val Lys His Ile Leu Asn Met
357 GCC GCC CTC CCA AAG GAT GTA CCC AAC AGC TCT CAG CCA GAG ATG GTG GAG GCC CTT GTC AAG CAC ATT TTA AAC ATG
              40                                                    60
    Leu His Leu Lys Lys Arg Pro Asp Val Thr Gln Pro Val Pro Lys Ala Ala Leu Leu Asn Ala Ile Arg Lys Leu
432 CTG CAC TTG AAG AAG AGA CCC GAT GTC ACC CAG CCG GTA CCC AAG GCG GCG CTT CTG AAC GCG ATC AGA AAG CTT
                                                        80
    His Val Gly Lys Val Gly Glu Asn Gly Tyr Val Glu Ile Glu Asp Asp Ile Gly Arg Arg Ala Glu Met Asn Glu
507 CAT GTG GGC AAA GTC GGG GAG AAC GGG TAT GTG GAG ATA GAG GAT GAC ATT GGA AGG AGG GCA GAA ATG AAT GAA
                90                                      100                               110
    Leu Met Glu Gln Thr Ser Glu Ile Ile Thr Phe Ala Glu Ser Gly Thr Ala Arg Lys Thr Leu His Phe Glu Ile
582 CTT ATG GAG CAG ACC TCG GAG ATC ATC ACG TTT GCC GAG TCA GGA ACA GCC AGG AAG ACG CTG CAC TTC GAG ATT
```

Fig. 8B.

```
                                                                                          130
         Ser Lys Glu Gly Ser Asp Leu Ser Val Val Glu Arg Ala Glu Val Trp Leu Phe Leu Lys Val Pro Lys Ala Asn
     657 TCC AAG GAA GGC AGT GAC CTG TCA GTG GTG GAG CGT GCA GAA GTC TGG CTC TTC CTA AAA GTC CCC AAG GCC AAC
                             140                                          150                                          160
         Arg Thr Lys Val Thr Ile Arg Leu Phe Gln Lys His Pro Gln Gly Ser Leu Asp Thr Gly Glu
     732 AGG ACC AAA GTC ACC ATC CGC CTC TTC CAG AAG CAC CCG CAG GGC AGC TTG GAC ACA GGG GAA
         Glu Ala Glu Glu Val Gly Leu Lys Gly Glu Arg Ser Glu Leu Ser Glu Lys Val Val Asp Ala Arg Lys
     807 GAG GCC GAG GAA GTG GGC TTA AAG GGG GAG AGG AGT GAA CTG TCT TCT GAA AAA GTA GAC GCT CGG AAG
                             190                                          200                                          210
         Ser Thr Trp His Val Phe Pro Val Ser Ser Ser Ile Gln Arg Leu Leu Asp Gln Gly Lys Ser Ser Leu Asp Val
     882 AGC ACC TGG CAT GTC TTC CCT GTC TCC AGC ATC CAG CGG TTG CTG GAC CAG GGC AAG AGC TCC CTG GAC GTT
         Arg Ile Ala Glu Gln Glu Ser Gly Ala Ser Leu Val Leu Gly Lys Lys Lys Lys Glu
     957 CGG ATT GCC TGT CAG GAG AGT GGC GCC TTG GTT CTC GGG AAG AAG AAG AAG GAG
                             240                                          250                                          260
         Glu Gly Gly Gly Lys Lys Gly Gly Gly Ala Asp Gly Glu Lys Glu Gln Ser His Arg
    1032 GAG GGG GGA GGG AAA AAG GGC GGT GGA GCA GAT GGA GAG AAG GAG CAG TCG CAC AGA
```

Fig. 8C.

```
                                                                                    →βA subunit
        Pro Phe Leu Met Leu Gln Ala Arg Gln Ser Glu Asp His Pro His Arg Arg Arg Arg Gly Leu Glu Cys Asp
1107    CCT TTC CTC ATG CTG CAG GCC CGG CAG TCT GAA GAC CAC CCT CAT CGC CGG CGT CGG GGC TTG GAG TGT GAT
                                       270                                                        310
        Gly Lys Val Asn Ile Cys Cys Lys Lys Gln Phe Phe Val Ser Phe Lys Asp Ile Gly Trp Asn Asp Trp Ile Ile
1182    GGC AAG GTC AAC ATC TGC TGC AAG AAA CAG TTC TTT GTC AGT TTC AAG GAC ATC GGC TGG AAT GAC TGG ATC ATT
                       290                                                        330
        Ala Pro Ser Gly Tyr His Ala Asn Tyr Cys Glu Gly Glu Cys Pro Ser His Ile Ala Gly Thr Ser Gly Ser Ser
1257    GCT CCC TCT GGC TAT CAT GCC AAC TAC TGC GAG GGT GAG TGC CCG AGC CAT ATA GCA GGC ACG TCC GGG TCC TCA
                               320                                                        360
        Leu Ser Phe His Ser Thr Val Ile Asn His Tyr Arg Met Arg Gly His Ser Pro Phe Ala Asn Leu Lys Ser
1332    CTG TCC TTC CAC TCA ACA GTC ATC AAC CAC TAC CGC ATG CGG GGC CAT AGC CCC TTT GCC AAC CTC AAA TCG
                       340                                                        380
        Cys Val Pro Thr Lys Leu Arg Pro Met Ser Met Leu Tyr Tyr Asp Asp Gly Gln Asn Ile Ile Lys Lys Asp Ile
1407    TGT GTG CCC ACC AAG CTG AGA CCC ATG TCC ATG TTG TAC TAT GAT GAT GGT CAA AAC ATC ATC AAA AAG GAC ATT
                       390                                          398
        Gln Asn Met Ile Val Glu Glu Cys Gly Cys Ser AM*
1482    CAG AAC ATG ATC GTG GAG GAG TGT GGG TGT TCA TAG AGTTGCCCAGCCCAGGGGGAAAGGGAGCAAGAGTTGTCCAGAGAAGACAGTG
1570    GCAAAATGAAGAGAATTTTTAAGGTTTCTGAGTTAACCAGAAAAATAGAAATTAAAAACAAAACA polyA
```

Fig. 9A.

```
                 7   Cys Thr Ser Cys Gly Gly Phe Arg Arg Pro Glu Glu Leu Gly Arg Val Asp Gly Asp Phe Leu Glu Ala Val
                                                          20                                              30
  1  CC           TGT ACG TCG TGC GGC GGC TTC CGG CGG CCA GAG GAG CTC GGC CGA GTG GAC GGC GAC TTC CTG GAG GCG GTG

Lys Arg His Ile Leu Ser Arg Leu Gln Met Arg Gly Arg Pro Lys Ala Val Pro Lys Ala Val His Ala Ala Met
                              40                                  50
 75  AAG CGG CAC ATC TTG AGC CGC CTG CAG ATG CGG GGC CGG CCC AAG GCC GTG CCT AAG GCC GTG CAC GCC GCC ATG

Val Thr Ala Leu Arg Lys Leu His Ala Gly Lys Val Arg Glu Arg Val Asp Gly Arg Val Glu Ile Pro His Leu Asp Gly
                              60                                  70                                  80
150  GTC ACG GCC CTG CGC AAG CTG CAC GCG GGC AAG GTG CGC GAG CGC GTG GAC GGC CGC GTG GAG ATC CCG CAC CTC GAC GGC

His Ala Ser Pro Gly Ala Asp Gly Gln Glu Arg Val Ser Ile Ile Ser Phe Ala Glu Thr Asp Gly Leu Ala
                              90                                  100                             130
225  CAC GCC AGC CCG GGC GCC GAC GGC CAG GAG CGC GTT TCC ATC ATC AGC TTC GCC GAG ACA GAT GGC CTC GCC

Ser Ser Arg Val Arg Leu Tyr Phe Phe Ile Ser Asn Gln Asn Leu Phe Val Val Gln Ala Ser Leu
                              110                                 120
300  TCC TCC CGG GTC CGG CTA TAC TTC TTC ATC TCC AAC CAG AAC CTG TTT GTG GTC CAG GCC AGC CTG

Trp Leu Tyr Leu Lys Leu Leu Pro Tyr Val Leu Glu Lys Gly Ser Arg Arg Lys Val Arg Val Lys Val Tyr Phe
                              140                                 150
375  TGG CTT TAC CTG AAA CTC CTG CCC TAC GTC CTG GAG AAG GGC AGC CGG CGG AAG GTG CGG GTC AAA GTG TAC TTC

Gln Glu Gln Gly His Gly Asp Arg Trp Asn Met Val Glu Lys Arg Val Asp Leu Lys Arg Ser Gly Trp His Thr
                              160                                 170                                 180
450  CAG GAG CAG GGT CAC GGC GAC AGG TGG AAC ATG GTG GAG AAG AGG GTG GAC CTC AAG CGC AGC GGC TGG CAT ACC
```

Fig.9B.

```
              Phe Pro Leu Thr Glu Ala Ile Gln Ala Leu Phe Glu Arg Gly Glu Arg Leu Asn Leu Asp Val Gln Cys Asp
       525    TTC CCA CTC ACG GAG GCC ATC CAG GCC TTG TTT GAG CGG GGC GAG CGA CTC AAC CTA GAC GTG CAG TGT GAC
                                  190                              200                              230
              Ser Cys Gln Glu Ala Val Pro Val Phe Val Asp Pro Gly Glu Glu Ser His Arg Pro Phe Val Val
       600    AGC TGC CAG GAG CTG GCC GTG CCG TTC GTG GAC CCA GGG GAA GAG TCG CAC CGG CCC TTT GTG GTG
                          210                              220       β_B subunit →
              Gln Ala Arg Leu Gly Asp Ser Arg His Arg Ile Arg Lys Arg Gly Leu Glu Asp Gly Arg Thr Asn Leu Cys
       675    CAG GCT CGG CTG GGC GAC AGC AGG CAC CGC ATT CGG AAG CGA GGC CTG GAG GAT GGC CGG ACC AAC CTC TGT
                                   240                             260                              280
              Arg Gln Gln Phe Phe Ile Asp Phe Arg Leu Ile Gly Trp Asn Asp Trp Ile Ile Ala Pro Thr Gly Tyr Tyr
       750    AGG CAA CAG TTC TTC ATT GAC TTC CGC CTC ATC GGC TGG AAC GAC TGG ATC ATA GCA CCC ACC GGC TAC TAC
                                   260                                  270                              300
              Gly Asn Tyr Cys Glu Gly Ser Cys Pro Ala Tyr Leu Ala Gly Val Pro Gly Ser Ala Ser Ser Phe His Thr Ala
       825    GGG AAC TAC TGT GAG GGC AGC TGC CCA GCC TAC CTG GCA GGG GTC CCC GGC TCT GCC TCC TCC TTC CAC ACG GCT
                          310                              320                              330
              Val Val Asn Gln Tyr Arg Met Arg Gly Leu Asn Pro Gly Thr Val Asn Ser Cys Cys Ile Pro Thr Lys Leu Ser
       900    GTG GTG AAC CAG TAC CGC ATG CGG GGT CTG AAC CCC GGC ACG GTG AAC TCC TGC TGC ATT CCC ACC AAG CTG AGC
                                   340                              350
              Thr Met Ser Met Leu Tyr Phe Asp Asp Glu Tyr Asn Ile Val Lys Arg Asp Val Pro Asn Met Ile Val Glu Glu
       975    ACC ATG TCC ATG CTG TAC TTC GAT GAT GAG TAC AAC ATC GTC AAG CGG GAC GTG CCC AAC ATG ATT GTG GAG GAG
```

Fig. 9C.

```
        Cys Gly Cys Ala OP*
             359
1050    TGC GGC TGC GCC TGA CAGTGCAAGGCAGGGGCACGGTGGGGCACGGAGGGGCAGTCCCGGGTGGGGCTTCTTCCAGCCCCGGGAACGGGGT
1145    ACACGGTGGGCTGGGCTGTGAGTACAGTCATTCTGTTGGGCTGTGGGAGATAGTGCCAGGGCCTGAGATATTTTCTACAGCTTCATAGAGCAACCAGTCAAA
1245    ACCAGAGCGAGAACCCTCAACTGCGTGACATGAAATACTTTAAAATGCACACGGCCACACGCCATCCTGCCACACACAGCAGCCTCCAGGA
1345    TACCAGCAAATGGATGCGTGACAAATGGCAGCTTAGCTACAAATGCCTGTCAGTCGGAGAGAATGGGGTGAGCAGCACCATTCCACCAGCTGGCCCGG
1445    CCACGTCTCGAAGTTGCGCTTCGGCCAGCTCGGCGAGCCTGCGTGCCCGGAGCAGCCACGGAGAGACGGGAAAAGCAGATGCAGGG
1545    GTGGGAGCGCAGCTCGGGGAGCCTGTCCTTCCATGCCCGGAGCCTGCGATGTCTGCTTCCCAGCTGGGATCCTT
1645    CGTGCTTCAAGGCCTGGGCTGTTTGTGGCCTTGACGACTTATGTGTGTTTGGGGTGGGAGGGGAGAAGAGGGGCTAAATTTGAT
1745    GACCGTTTGACTGTTTGTGCCTGTTGGGCTTGACGACTTATGTGTGTTTGGGGTGGGAGGGGAGAAGAGGGGCTAAATTTGAT
1845    GCTTTAACTGATCTCCAACAGTTGACAGGTCATCCTTGCCAGTTGTATAACTGAAAAAGGACTTTTCTACCAGGTATGACCTTTTAAGTGAAAATCTGAA
1945    TTGTTCTAAATGAAAAGAAAAA
```

NUCLEIC ACID ENCODING THE ALPHA CHAIN PRODOMAINS OF INHIBIN AND METHOD FOR SYNTHESIZING POLYPEPTIDES USING SUCH NUCLEIC ACID

This is a divisional application of U.S. Ser. No. 07/744,207 filed Aug. 12, 1991, now U.S. Pat. No. 5,215,893, which is a divisional application of U.S. Ser. No. 07/215,466 filed Jul. 5, 1988, now U.S. Pat. No. 5,089,396, which is a divisional application of U.S. Ser. No. 06/906,729 filed Dec. 31, 1986, now U.S. Pat. No. 4,798,885, which is a continuation-in-part application of U.S. Ser. No. 06/827,710 filed Feb. 7, 1986, now abandoned, which is a continuation-in-part application of U.S. Ser. No. 06/783,910 filed Oct. 3, 1985, now abandoned.

BACKGROUND

This invention relates to methods for making proteins in recombinant cell culture which contain the α or β chains of inhibin. In particular, it relates to methods for obtaining and using DNA which encodes inhibin, and for making inhibin variants that depart from the amino acid sequence of natural animal or human inhibins and the naturally-occurring alleles thereof.

Inhibin is a protein produced in the gonad which acts specifically at the pituitary level to inhibit the secretion of follicle-stimulating hormone (FSH). The existence of inhibin was first postulated by McCullagh in 1932 ("Science" 76: 19–20). Such preferential regulation of the gonadotropin secretion has generated a great deal of interest and has prompted many laboratories in the past fifty years to attempt to isolate and characterize this substance from extracts of testis, spermatozoa, rete testis fluid, seminal plasma and ovarian follicular fluid, using various bioassays. Although many reports have appeared in the literature claiming the purification of inhibin-like material with molecular weights ranging from 5,000 to 100,000 daltons, subsequent studies have shown that these substances were not homogeneous, did not have the high specific activity expected of true inhibin and/or failed to exhibit the molecular characteristics of inhibin as described herein (de Jong, Inhibin-Factor Artifact, "Molecular & Cellular Endocrin." 13: 1–10 (1979); Sheth et al., 1984, "F.E.B.S." 165(1) 11–15; Seidah et al., 1984, "F.E.B.S." 175(2): 349–355; Lilja et al., March 1985, "F.E.B.S." 182(1): 181–184; Li et al., June 1985, "Proc. Nat. Acad. Sci. USA" 82: 4041–4044; Seidah et al., "F.E.B.S." 167(1): 98–102; and Beksac et al., 1984, "Intern. J. Andrology" 7: 389–397).

A polypeptide having inhibin activity was purified from bovine or ovine follicular fluid (PCT 86/00078, published Jan. 3, 1986). This protein was reported to have a molecular weight of 56,000±1,000 on SDS-PAGE and was dissociable into two subunits having apparent molecular weights of 44,000±3,000 and 14,000±2,000. Amino terminal sequences for each subunit were described.

Two proteins both having a molecular weight of about 32,000 daltons and having inhibin activity have been successfully isolated from porcine follicular fluid. Purification of porcine inhibin to substantial homogeneity, i.e., about 90% by weight of total protein in the fraction, was achieved through a combination of protein separation procedures including heparin-Sepharose affinity chromatography, gel filtration and reverse-phase, high-performance liquid chromatography (RP-HPLC).

These proteins were isolated to substantial homogeneity from material obtained from swine and are referred to as Protein A and Protein B. Each protein has a molecular weight of about 32,000 daltons (32 K) and is composed of two polypeptide chains having molecular weights of 18,000 and 14,000 daltons, respectively, the chains being linked together in the hormonally active protein by disulfide bonding. The amino-terminal amino acid residue sequence of the 18,000 dalton (18 K) or alpha chain of both proteins was determined to be Ser-Thr-Ala-Pro-Leu-Pro-Trp-Pro-Trp-Ser-Pro-Ala-Ala-Leu-Arg-Leu-Leu-Gln-Arg-Pro-Pro-Glu-Glu-Pro-Ala-Val. The amino-terminal amino acid residue sequence of the 14,000 dalton (14 K) or beta chain of Protein A was determined to be Gly-Leu-Glu-X-Asp-Gly-Lys-Val-Asn-Ile-X-X-Lys-Lys-Gln-Phe-Phe-Val-Ser-Phe-Lys-Asp-Ile-Gly-Trp-Asn-Asp-Trp-Ile-Ile-Ala and of Protein B was determined to be Gly-Leu-Glu-X-Asp-Gly-Arg-Thr-Asn-Leu-X-X-Arg-Gln-Gln-Phe-Phe-Ile-Asp-Phe-Arg-Leu. Proteins A and B have been completely characterized. Each 32 K protein exhibits inhibin activity in that it specifically inhibits the basal secretion of FSH but does not inhibit secretion of luteinizing hormone (LH). The individual chains were not hormonally active.

After the filing of the parent application hereto, inhibin B-chain dimers were shown to exist in follicular fluid as naturally-occurring substances, termed activin, which are capable of stimulating FSH release by rat anterior pituitary cells (Vale et al., 1986, "Nature" 321: 776–779 and Ling et al., 1986, "Nature" 321: 779–782).

The amino acid sequence of the α and β chains of inhibin from humans remained unknown until the invention herein. The large quantities of human follicular fluid required to parallel the studies conducted with animal inhibins are not readily available, nor is there any assurance that human and animal inhibins would be sufficiently similar that purification using a parallel procedure would be effective. Accordingly, methods are needed for determining the characteristics and amino acid sequence for human inhibin.

Also needed are economical methods for making the α and β chains of inhibin in large quantities, preferably entirely and completely free of proteins from the species homologous to the inhibin in question, which inhibin preferably also is biologically active.

These and other objects will be apparent from consideration of the invention as a whole.

SUMMARY

Nucleic acid now has been isolated and cloned in replicable vectors which encodes the mature porcine and human α and β chains of inhibin and their precursor prepro and pro forms. Sequencing of inhibin-encoding cDNA has led to the identification of prodomain regions located N-terminal to the mature inhibin chains that represent coordinately expressed biologically active polypeptides. The prodomain regions or prodomain immunogens are useful in monitoring preproinhibin processing in transformant cell culture or in experiments directed at modulating the clinical condition or reproductive physiology of animals. Thus α or β chain nucleic acid is used to prepare prodomain sequences from the precursor forms of the inhibin chains, to transform host cells for the recombinant expression of mature inhibin α and/or β chains, and in diagnostic assays.

In particular, regions from inhibin α and/or β chains are expressed in recombinant cell culture by a method comprising ligating the nucleic acid encoding the region into a replicable vector under the control of a promoter, transforming a host cell with the vector, culturing the host cell and recovering the prodomain, activin or inhibin from the cultured cell. Inhibin, activin and prodomains produced by the method of this invention are entirely free of homologous source proteins and can be produced in biologically active form.

The nucleic acids identified herein encode the α, $β_A$ and $β_B$ chains of porcine or human inhibin. Recombinant cells are transformed to express $αβ_A$ or $αβ_B$ inhibins, or to express β-chain heterodimers or homodimers (which are collectively referred to in the literature as activin). β-chain dimers as products of recombinant cell expression are free of homologous proteins with which they ordinarily are associated in nature.

Inhibin or activin and their nontoxic salts, combined with a pharmaceutically acceptable carrier to form a pharmaceutical composition, are administered to mammals, including humans, for control of fertility. Administration of inhibin decreases fertility in female mammals and decreases spermatogenesis in male mammals, and administration of a sufficient amount induces infertility. Inhibin is also useful in tests to diagnose infertility. Activin has been shown in the literature to be capable of stimulating FSH release from pituitary cells and accordingly is useful as a fertility inducing therapeutic.

The method of this invention also facilitates the convenient preparation of inhibin, activin and prodomain variants having primary amino acid sequences and/or glycosylation differing from the native analogues, in particular fusions of immunogenic peptides with inhibin, activin or prodomain sequences.

BRIEF DESCRIPTION OF THE DRAWINGS

FIGS. 1B (I)-(II) shows the nucleotide and predicted amino acid sequence of the porcine inhibin α-chain precursor. Nucleotides are numbered at the left and amino acids are numbered throughout. The amino acid sequence underlined was used to design a long synthetic DNA probe. The 364 amino acid precursor includes a hydrophobic signal sequence, a pro-region, and the mature α-chain (amino acids 231-364). The proteolytic processing site Arg-Arg (black bar) immediately precedes the NH$_2$-terminus of the mature alpha chain. Several other putative dibasic processing sites present in the pro-region are indicated by open bars. The single potential N-linked glycosylation site is shown by the cross-hatched bar. The AATAAA box close to the 3' end of the mRNA is underlined.

FIGS. 2B (I)-(IV) is the nucleotide sequence and deduced amino acid sequence of the porcine inhibin β-subunit precursors. The $β_B$ sequence is aligned with the $β_A$ sequence for maximum homology. The NH$_2$-termini of the β-subunit precursors are indicated by bracket and arrows. Cysteine residues are shaded, possible processing sites are indicated by open bars, and a potential glycosylation site is shown by the cross-hatched box. A very GC-rich region present 3' to the termination codon intron sequences is underlined and overlined in both sequences. Amino acid sequences used to design oligonucleotide probes are underlined, as is the AATAAA polyadenylation signal. There was one nucleotide difference between λPIN-$β_A$8 and other clones covering this area. A G-to-A change causes a change of amino acid 278 from a glycine to a serine. The proteolytic processing site Arg Arg Arg Arg Arg (black bar) immediately precedes the NH$_2$ terminus of the mature $β_A$ subunit, with the prosequences located upstream. The amino acids for the $β_A$ subunit only are numbered.

FIG. 3 is a Northern blot analysis of porcine ovarian mRNA with α, $β_A$ and $β_B$ subunit cDNA hybridization probes. Lanes a, b, c, d, and f are polyA+ mRNA and e and g are total RNA. The position of the 28S and 18S ribosomal RNAs are shown. Lanes a, d, and e were hybridized with an α-subunit cDNA probe; lanes d, e and g with a $β_A$ subunit specific probe, and lane c with a $β_B$ subunit specific probe. The α-subunit mRNA is approximately 1.5 kb, the $β_A$ subunit mRNAs are approximately 4.5 kb. The hybridizations shown in lanes a, b, and c were performed with probes of approximately equal length and specific activity in order to judge relative mRNA levels.

FIG. 4A is a comparison of the human β-TGF amino acid sequence and porcine inhibin $β_A$ and $β_B$ amino acid sequences. The sequences were aligned around the cysteine residues. Identical residues are boxed, while conservative changes are designated by an asterisk.

FIG. 4B compares the α-subunit sequence with the $β_A$-inhibin sequence.

FIGS. 6A-B shows the nucleotide sequence and deduced amino acid sequence of the human α-inhibin cDNA. The 335 amino acid pro- or inhibin sequence is numbered from the hypothesized signal cleavage site. Sixteen amino acids of the signal sequence are numbered −1 through −16. Homology with the porcine sequence predicts a further 12 amino acid residues in the signal sequence. In this and other figures, putative dibasic processing sites are shown by the open bars, glycosylation sites indicated by cross-hatched bars, and amino terminal mature chain processing sites are depicted as black bars. The poly(A) additional signal sequence is underlined. Cysteine residues are shaded.

FIGS. 7A-B is a comparison of the human and porcine α-inhibin protein sequences. Spaces are introduced to maximize the homology; positions of non-identity are indicated by stars. Numbering is as for the porcine sequence, which is one amino acid shorter than the human.

FIGS. 8A–C shows that the nucleotide and deduced amino acid sequence of the human $\beta_A$ inhibin signal sequence (residues −28 through −1) is 28 amino acids with the precursor being 378 amino acids in length. The basic processing site is indicated by a black bar, and a potential glycosylation site in the precursor is indicated by a cross-hatched bar above the sequence. Cysteine residues are shaded.

FIGS. 9A–C illustrates the nucleotide and deduced amino acid sequence of human $\beta_B$ inhibin cDNA. The sequence commences at a cysteine residue (position 7), which lines up with the cysteine present at residue 7 in the $\beta_A$ sequence (see FIG. 8). The processing site for the mature $\beta_B$ inhibin is shown as a black bar and a potential glycosylation site as a cross-hatched bar. Cysteine residues are shaded.

DETAILED DESCRIPTION

Figure 1A:
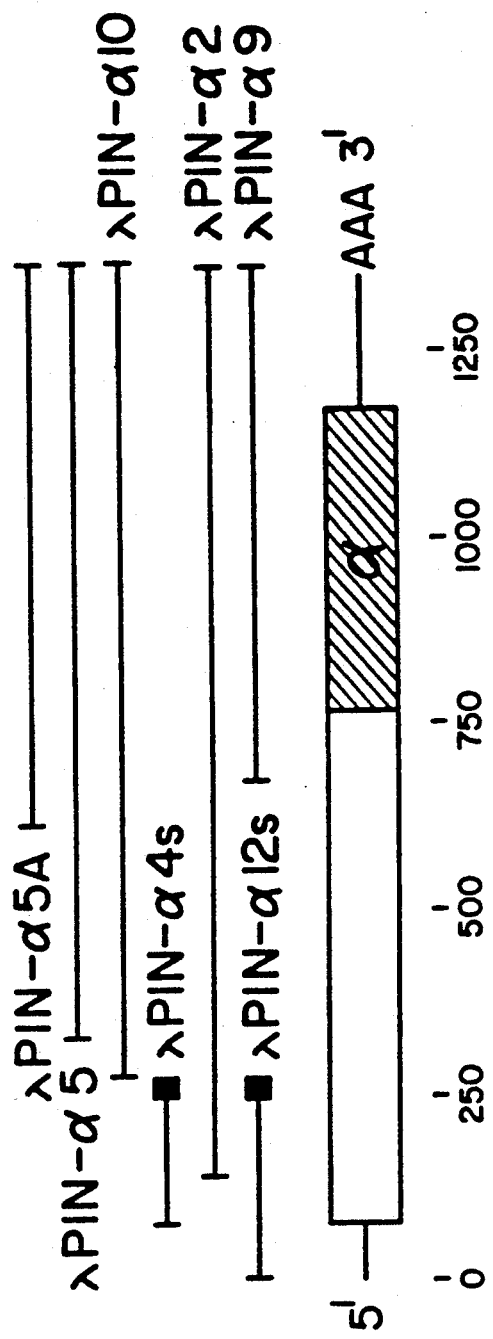
FIG. 1A is a schematic representation of the porcine α-chain mRNA. Overlapping cDNA clones used in the sequence determination are shown above the diagram of the mRNA structure. Black boxes on the 3' ends of λ clones indicate that these clones were obtained by specific priming. Untranslated sequences are represented by a line, coding sequences are boxed. The unfilled portion represents the coding region for the signal peptide and pro-sequences, and the cross-hatched area indicates the 134 amino acid α-chain. The scale is in nucleotides from the 5' end of the longest cDNA clone.

The polypeptides of this invention are the $\alpha$ and $\beta$ chains of inhibin, as well as their multimer forms (activin and inhibin), their prepro forms and their prodomains, together with glycosylation and/or amino acid sequence variants of each chain or form thereof. Inhibin (including alleles) from human or animal sources inhibits the basal release of FSH but not of LH from anterior pituitary cells while activin does the opposite (hereinafter referred to as "hormonally active" activin or inhibin).

Generally, amino acid sequence variants will be substantially homologous with the relevant portion of the porcine or human $\alpha$ or $\beta$ chain sequences set forth in FIGS. 1B, 2B, 6, 8 and 9. Substantially homologous means that greater than about 70% of the primary amino acid sequence of the candidate polypeptide corresponds to the sequence of the porcine or human chain when aligned in order to maximize the number of amino acid residue matches between the two proteins. Alignment to maximize matches of residues includes shifting the amino and/or carboxyl terminus, introducing gaps as required and/or deleting residues present as inserts in the candidate. For example, see FIGS. 2B and 7 where the $\beta_A$ and $\beta_B$ subunits for human and porcine $\alpha$-inhibin sequences are aligned for maximum homology. Typically, amino acid sequence variants will be greater than about 90% homologous with the corresponding native sequences shown in FIGS. 1B, 2B, 6, 8 and 9.

Variants that are not hormonally-active fall within the scope of this invention, and include polypeptides that may or may not be substantially homologous with either a mature inhibin chain or prodomain sequence, but which are 1) immunologically cross-reactive with antibodies raised against the native counterpart or 2) capable of competing with such native counterpart polypeptides for cell surface receptor binding. Hormonally inactive variants are produced by the recombinant or organic synthetic preparation of fragments, in particular the isolated $\alpha$ or $\beta$ chains of inhibin, or by introducing amino acid sequence variations so that the molecules no longer demonstrate hormonal activity as defined above.

Immunological or receptor cross-reactivity means that the candidate polypeptide is capable of competitively inhibiting the binding of the hormonally-active analogue to polyclonal antisera raised against the hormonally-active analogue. Such antisera are prepared in conventional fashion by injecting goats or rabbits S.C. with the hormonally-active analogue or derivative in complete Freunds adjuvant, followed by booster intraperitoneal or S.C. injections in incomplete Freunds.

Variants that are not hormonally active but which are capable of cross-reacting with antisera to hormonally-active inhibin, activin, or prodomains are useful (a) as reagents in diagnostic assays for the native analogues or their antibodies, (b) when insolubilized in accord with known methods, as an agent for purifying anti-native analogue antibodies from antisera, and (c) as an immunogen for raising antibodies to hormonally-active analogues.

This invention includes the pro and/or prepro sequences of the inhibin $\alpha$ or $\beta$ chain precursors, or their immunologically or biologically active fragments, substantially free of the corresponding mature inhibin chains. These sequences for porcine and human inhibin are shown in FIGS. 1B, 2B, 6, 8 and 9. The prepro sequence for the porcine $\alpha$ subunit precursor is the polypeptide comprised by residues 1 to about 230, while the $\beta_A$ subunit pro sequence is comprised by residues 1 to about 308. These sequences shall be referred to herein as encompassing prodomain sequences.

The $\alpha$ and $\beta$ subunit prodomain sequences are comprised of several domains bounded by proteolysis sites, any one of which is synthesized herein separately or in combination with other domains. The principal porcine $\beta_A$ domains fall within residues 1 to about 70 (domain I), about 70 to about 110 (domain II), about 110 to about 180 (domain III), about 180 to about 260 (domain IV), and about 270 to about 309 (domain V). In particular, the porcine $\beta_A$ domains are GHSAAPDCP-SCALATLPKDVPNSQPEMVEAV, HILNMLHLKKRPDVTQPVPKAALLNAI, LHVGKVGENGYVELEDDIG, AEMNELMEQT-SEIITFAEAGRARKTLRFEISKEGSDLSVVERA-EIWLFKVPKANRTRTKV SIRLFQQQ, PQGSADAGEEAEDVGFPEEKSEVLISEKV-VDA, STWHIFPVSSSIQRLLDQGKSALDIR-TACEQCHETGASLVLLG, and GHSAAPDCP-SCALATLPKDVPNSQPEMVEAVK-KHILNMLHLKKRPDVTQPVPKAALLNAI. The porcine $\beta_B$ domains comprise RAAHILL-HAVRVSGWLNL as well as homologous $\beta$ domains having the same sequences. The porcine $\alpha$ domains comprise GPELDRELVLAKVRALFLDALG-PPAVTGEGGDPGV and GSEPEEEDVSQAIL-PATGARCGAEPAAGELAREAEEGL-FTYVGRPSQHTHSRQVTSAQLWFHTGL DRQGMAAANSSGPLLDLLALSSRG-PVAVPMSLGQAPPRWAVL-HLAASALPLLTHPVLVLLLRCPLC SCSAR-PEATPFLVAHTRARPPSGGERA. A typical combination domain polypeptide would be $\beta_A$ domain II linked at its C-terminus to the NH$_2$-terminus of $\beta_A$ domain III. In addition, these domains are fused together by the proteolysis sites found in the sequences shown in FIGS. 1B or 2B, by 1 to 4 residue polypeptides that are resistant to hydrolysis (for example, glutaminyl or histidyl residues), or are directly fused, whereby, in all three instances, combination domain polypeptides are produced.

Principal human $\alpha$ chain prodomains are approximately residues 30–199 and 1 to 29, human $\beta A$ prodomains are approximately residues 1–30, 32–40, 43–59, 62–80, 83–185 and 186–230 while human $\beta_B$ prodomains are approximately residues 1-13, 15-30, 32-59, 62-145, 148-195 and 198-241 (referring to the numbering system adopted in FIGS. 6, 8 and 9, respectively). Combination prodomain polypeptides are within the scope hereof, for example, the $\beta_A$ prodomain at about 43-80, and the $\beta_B$ prodomains at about 1-30 and about 32-145. The preferred human $\alpha$, $\beta_A$ and $\beta_B$ chain prodomains are about residues 1-29, about 43-80 and about 1-30, respectively.

The intact isolated prepro or prodomain $\beta_A$, $\beta_B$ or $\alpha$ sequences are best synthesized in recombinant cell culture. The individual subcomponent domains are synthesized by routine methods of organic chemistry or by recombinant cell culture. They then are labelled with a radioisotope or other detectable group such as an enzyme or fluorophore in accord with known methods and used in standard competitive immunoassays to detect the levels of prepro or pro forms of inhibin, including individual domains, in transformants with DNA encoding such forms or their precursors. This assay is useful in determining whether proteolytic hydrolysis of proinhibin is occurring in the host transformants or their culture media. The assay also is useful in determining whether a rate limiting step in recombinant synthesis is translation of mRNA into the prepro forms or processing of the prepro forms into mature inhibin. For example, high levels of prepro or pro inhibin in cell lysates, but relatively low levels of secreted mature inhibin, would suggest that the host cell is adequately transcribing and translating the inhibin DNA, but is not processing the precursors at an adequate rate. Thus, in this case one would select an alternate host cell rather than concentrating on improving the transcription or translation efficiency of the transforming plasmid, e.g., by selecting an alternative promoter. The prodomain sequences also are believed to be involved in coordinate modulation of animal physiology in reproductive cycles and fertility.

Amino acid sequence variants are any one of 1) hormonally-active, 2) cross reactive with antibodies raised against mature inhibin or prodomain $\alpha$ or $\beta$ chain sequences, or 3) cross-reactive with inhibin/activin cell surface receptors, but are characterized by a primary amino acid sequence that departs from the sequence of natural inhibins or prodomain sequences. These derivatives ordinarily are preprepared by introducing insertions, deletions or substitutions of nucleotides into the DNA encoding the target DNA to be modified in order to encode the variant, and thereafter expressing the DNA in recombinant cell culture. Polypeptides having up to about 100-150 residues also are conveniently prepared by in vitro synthesis. Such variants are characterized by the predetermined nature of the variation, a feature that sets them apart from naturally occurring allelic or interspecies variation. The variants may exhibit the same qualitative biological activity as the naturally-occurring analogue or may act antagonistically towards such analogues.

While the site for introducing a sequence variation is predetermined, it is unnecessary that the mutation per se be predetermined. For example, in order to optimize the performance of mutation at a given site, random mutagenesis may be conducted at the target codon or region and the expressed inhibin mutants screened for the optimal combination of desired activity. Techniques for making substitution mutations at predetermined sites in DNA having a known sequence is well known, for example M13 primer mutagenesis.

Mutagenesis is conducted by making amino acid insertions, usually on the order of about from 1 to 10 amino acid residues, or deletions of about from 1 to 30 residues. Deletions or insertions preferably are made in adjacent pairs, i.e. a deletion of 2 residues or insertion of 2 residues. Substitutions, deletions, insertions or any subcombination may be combined to arrive at a final construct. Insertions include amino- or carboxyl-terminal fusions, e.g. a hydrophobic extension added to the carboxyl terminus. Preferably, however, only substitution mutagenesis is conducted. Obviously, the mutations in the encoding DNA must not place the sequence out of reading frame and preferably will not create complementary regions that could produce secondary mRNA structure.

Not all mutations in the DNA which encode the polypeptides herein will be expressed in the final secreted product. For example, a major class of DNA substitution mutations are those in which a different secretory leader or signal has been substituted for the native porcine or human $\alpha$ or $\beta$ chain secretory leader, either by deletions within the leader sequence or by substitutions, wherein most or all of the native leader is exchanged for a leader more likely to be recognized by the intended host. For example, in constructing a procaryotic expression vector the porcine or human $\alpha$ or $\beta$ chain secretory leader is deleted in favor of the bacterial alkaline phosphatase or heat stable enterotoxin II leaders, and for yeast the leader is substituted in favor of the yeast invertase, alpha factor or acid phosphatase leaders. However, the porcine and human secretory leaders are recognized by many heterologous higher eukaryotic cells. When the secretory leader is "recognized" by the host, the host signal peptidase is capable of cleaving a fusion of the leader polypeptide fused at its C-teminus to the mature inhibin or prodomain such that mature inhibin or prodomain polypeptide is secreted.

Another major class of DNA mutants that are not expressed in final form as amino acid sequence variations are nucleotide substitutions made in the DNA to enhance expression, primarily to avoid 5' stem and loop structures in the transcribed mRNA (see de Boer et al., EP 75,444A) or to provide codons that are more readily transcribed by the selected host, e.g. the well-known preference codons for $E.$ $coli$ or yeast expression. These substitutions may or may not encode substituted amino acid residues, but preferably do not.

Insertional and deletional amino acid sequence variants are proteins in which one or more amino acid residues are introduced into or removed from a predetermined site in the target inhibin, activin, prodomain or proform of inhibin or activin. Most commonly, insertional variants are fusions of heterologous proteins or polypeptides to the amino or carboxyl terminus of the $\alpha$ or $\beta$ chains, the prodomains or other inhibin derivatives. Immunogenic derivatives are made by fusing an immunogenic polypeptide to the target sequence, e.g. a prodomain polypeptide, by synthesis in vitro or by recombinant cell culture transformed with DNA encoding the fusion. Such immunogenic polypeptides preferably are bacterial polypeptides such as trpLE, beta-galactosidase and the like, together with their immunogenic fragments. Other insertions entail inserting heterologous eukaryotic (e.g. the herpes virus gD signal) or microbial secretion signal or protease processing sequences upstream from the $NH_2$-terminus of the protein to be secreted. Deletions of cysteine or other labile residues also may be desirable, for example in increasing the oxidative stability of the α or β chain. Deletional derivatives will produce α or β chain fragments. Such fragments, when biologically or immunologically active, are within the scope herein. For instance, a fragment comprising $\beta_B$ or $\beta_A$ residues about from 11 to 45 (numbered from mature $Gly_1$) is to be included within the scope herein.

Immunogenic conjugates of prodomain polypeptides, inhibin and activin are readily synthesized in recombinant cell culture as fusions with immunogenic polypeptides, e.g. beta-lactamase or viral antigens such as the herpes gD protein, or by preparation of the polypeptides in unfused form (by recombinant or in vitro synthetic methods) followed by covalent cross-linking to an immunogenic polypeptide such as keyhole limpet hemocyanin or STI using a divalent cross-linking agent. The immunogenic polypeptides are formulated with a vaccine adjuvant, e.g. alum or Freunds. Methods for preparing proteins in adjuvants and for cross-linking are well-known per se and would be employed by one skilled in the art, as are methods for vaccinating animals. The immunogenic conjugates are useful in preparing antibodies to the prodomain region for use in monitoring inhibin manufacture or for in vivo vaccination with the objective of raising antibodies capable of modulating animal physiology in reproductive cycles and fertility. Typically, the prodomain or its immunogen is administered in varied doses to fertile laboratory animals or swine and the reproductive cycles and fertility of the animals monitored, together with assays of serum levels of anti-immunogen or prodomain by routine competitive or sandwich immunoassay.

Substitution derivatives are produced by mutating the DNA in a target codon, so that thereafter a different amino acid is encoded by the codon, with no concomitant change in the number of residues present in the molecule expressed from the mutated DNA. Substitutions or deletions are useful for example in increasing the stability of the proteins herein by eliminating proteolysis sites, wherein residues are substituted within or adjacent to the sites or are deleted from the sites, or by introducing additional disulfide bonds through the substitution of cysteine for other residues. Substitutions are useful for facilitating the synthesis or recovery of mature or prodomain α or β chains. For example, methionine residues within the mature inhibin sequences are substituted or deleted, prepro sequences deleted, methionine is inserted at the −1 site immediately $NH_2$ terminal to the mature $NH_2$ terminal residue and another sequence inserted N-terminal to the exogenous methionine. The inhibin derivative in this case is expressed as a fusion having an intermediate methionyl residue, which in turn is cleaved at this residue by cyanogen bromide in accordance with known practice. The mature inhibin derivative released from the fusion is recovered.

Exemplary porcine inhibin derivatives are [$Asn_{266}$→Gln]Inhα (to remove the putative glycosylation site), [$Cys_{325}$ or $Cys_{324}$→Δ]Inhα, [$Cys_{361}$ or $Cys_{363}$→Δ]Inhα, [$Lys_{321}$ or $Lys_{322}$→Δ]Inh$\beta_A$ or [$Lys_{322}$→His or Ser]Inh$\beta_A$ (to inactivate a potential proteolysis site), [$Lys_{315}$→Arg; $Val_{316}$→Thr] Inh$\beta_A$ (to create a $\beta_A/\beta_B$ hybrid), [$Cys_{388}$ or $Cys_{390}$→Δ]Inh$\beta_A$, [$Lys_{411}$→Gln]Inh$\beta_A$, [$Arg_{315}$→Lys, $Val_{316}$→Thr]Inh$\beta_B$ (to create a $\beta_B/\beta_A$ hybrid), [$Cys_{319}$ or $Cys_{320}$→Δ]Inh$\beta_B$ [$Pro_{381}$ $Gly_{382}$→Pro Phe Gly]Inh$\beta_B$, and [$Arg_{395}$→Gln]Inh$\beta_B$, wherein Inh is an abbreviation for inhibin and the residue numbers for Inh$\beta_B$ are those used for the corresponding Inh$\beta_A$ residue (see FIG. 2B).

The h$\beta_A$ amino acid positions which are principal candidates for mutational substitution or deletion (or adjacent to which residues may be inserted) include residues 293–297, 364–376 and 387–398 (FIG. 8). Preferably, the proline, cysteine and glycine residues within these sequences are not modified. Candidates having greater potency than inhibin or activin, or which serve as inhibin or activin antagonists, are identified by a screening assay wherein the candidate is diluted into solutions containing constant amounts of inhibin or activin and the compositions are assayed in the rat pituitary cell assay. Candidates which neither antagonize or agonize inhibin or activin are screened for utility in immunoassays for inhibin or activin by measuring competitive immunodisplacement of labelled inhibin or activin of the native hormones from polyclonal antibody directed against the native hormones. Exemplary contemplated sequence variants of h$\beta_A$ include $Phe_{302}$→Ile or Leu; $Gln_{297}$→Asp or Lys; $Trp_{307}$→Tyr or Phe; $Trp_{310}$→Tyr or Phe; $Ile_{311}$→Phe or Val; $Tyr_{317}$→Trp or Thr; $His_{318}$→Lys; $Ala_{319}$→Ser; $Asn_{320}$→Gln, Tyr or His; $Tyr_{321}$→Thr or Asp, $Phe_{340}$→Tyr (a TGF-$\beta/\beta_A$ intrachain hybrid); $His_{353}$→Asp; $His_{353}$→Lys (a $\beta_A/\beta_B$ hybrid); $Phe_{356}$→Tyr; $Val_{364}$→Phe; $Val_{364}$→Leu; $Tyr_{375}$→Thr; $Tyr_{376}$→Trp; $Asn_{389}$→Gln, His or Lys; $Ile_{391}$→Leu or Thr; $Met_{390}$→Leu or Ser; $Val_{392}$→Phe, Glu, Thr or Ile. Comparable modifications are made in the human $\beta_B$ chain. For example, h$\beta_A$ contains a phenylalanyl residue at position 302, and h$\beta_B$ also contains a phenylalanyl residue at a homologous position (264, FIG. 9) when aligned in the same fashion as is shown for porcine $\beta_B$ in FIG. 4A. Thus, since the $Phe_{302}$ residue of $\beta_A$ is described above as substituted by isoleucinyl or leucinyl, the $Phe_{264}$ of $\beta_B$ is substituted with the same residues.

A factor in establishing the identity of a polypeptide as inhibin, activin or an inhibin variant is the ability of antisera which are capable of substantially neutralizing the hormonal activity of mature inhibin or activin to also substantially neutralize the hormonal activity of the polypeptide in question. However it will be recognized that immunological identity and hormonal activity are not necessarily coextensive. For example, a neutralizing antibody for inhibin may not bind a candidate protein because the neutralizing antibody happens to not be directed to specifically bind a site on inhibin that is critical to its activity. Instead, the antibody may bind an innocuous region and exert its neutralizing effect by steric hindrance. Therefore a candidate protein mutated in this innocuous region might no longer bind the neutralizing antibody, but it would nonetheless be inhibin in terms of substantial homology and biological activity.

It is important to observe that characteristics such as molecular weight, isoelectric point and the like for a native or wild type mature inhibin or activin obtained from follicular fluid or other tissue sources are descriptive only for the native form. Variants contemplated by the foregoing definition will include other polypeptides which will not exhibit all of the characteristics of native analogue. For example, inhibin derivatives like the insertion mutants, deletion mutants, or fusion proteins described above will bring inhibin outside of the molecular weight established for the corresponding native inhibin because fusion proteins with mature inhibin or proinhibin itself as well as insertion mutants will have a greater molecular weight than native, mature inhibin.

On the other hand, deletion mutants of native, mature inhibin will have a lower molecular weight. Finally, post-translational processing of preproinhibin chains in heterologous cell lines may not be accomplished with the fidelity exercised by the homologous host cell, thereby resulting in some variation in the amino termini of the α and/or β chains. This variation may be encountered as residual prosequence remaining with the mature protein, or the loss of several mature residues that are cleaved off with the prosequence. The same is true with processing of the preprotein in heterologous recombinant cells.

Covalent modifications of inhibin, activin or prodomains are included within the scope hereof and include covalent or aggregative conjugates with other chemical moieties. Covalent derivatives are prepared by linkage of functionalities to groups which are found in the inhibin amino acid side chains or at the N-or C-termini, by means known in the art. For example, these derivatives will include: aliphatic esters or amides of the carboxyl terminus or residues containing carboxyl side chains, e.g., aspartyl residues; O-acyl derivatives of hydroxyl group-containing residues such as seryl or alanyl; and N-acyl derivatives of the amino terminal amino acid or amino-group containing residues, e.g. lysine or arginine. The acyl group is selected from the group of alkyl moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups, e.g. m-maleimidobenzoyl-N-hydroxy succinimide ester. Preferred derivatization sites are at histidine residues.

Covalent or aggregative derivatives of mature inhibin, activin or prodomain sequences are useful as reagents in immunoassay or for affinity purification procedures. For example, inhibin or prodomain is insolubilized by covalent bonding to cyanogen bromide-activated Sepharose by methods known per se or adsorbed to polyolefin surfaces (with or without glutaraldehyde cross-linking) for use in the assay or purification of anti-inhibin or anti-prodomain antibodies or cell surface receptors. Inhibin or a prodomain sequence also is labelled with a detectable group, e.g., radioiodinated by the chloramine T procedure, covalently bound to rare earth chelates or conjugated to another fluorescent moiety for use in diagnostic assays, especially for diagnosis of inhibin or prodomain levels in biological samples by competitive-type immunoassays.

DNA which encodes the complete α and β chains of inhibin/activin is obtained by chemical synthesis, by screening reverse transcripts of mRNA from ovary, or by screening genomic libraries from any cell. It may be more efficient to simply synthesize portions of the DNA desired since screening is required to identify DNA in cDNA or genomic libraries that encode the α and β chains. Synthesis also is advantageous because unique restriction sites can be introduced at the time of preparing the DNA, thereby facilitating the use of the gene in vectors containing restriction sites otherwise not present in the native sequence, and steps can be taken to enhance translational efficiency as discussed above, without the need to further modify the DNA as by mutagenesis or the like. cDNA encoding the α or β chains is free of untranslated intervening sequences (introns) as well as free of flanking DNA encoding other proteins homologous to their source.

DNA encoding the α and β chains is obtained from other sources than porcine or human by (a) obtaining a cDNA library from the ovary of the target animal, (b) conducting Southern analysis with labelled DNA encoding porcine or human α and β chains or fragments thereof (generally, greater than 100 bp) in order to detect clones in the cDNA library that contain homologous sequences, (c) analyzing the clones by restriction enzyme analysis and nucleic acid sequencing so as to identify full-length clones and, if full length clones are not present in the library, recovering appropriate fragments from the various clones and ligating them at restriction sites common to the clones to assemble a clone encoding the full-length molecule. As shown infra, any sequences missing from the library can be obtained by the 3' extension on ovarian mRNA of synthetic oligodeoxynucleotides complementary to cDNA identified by screening the library, or homologous sequences are supplied from known animal cDNAs. This is particularly useful in constructing pre or prepro inhibin sequences to facilitate processing of preproinhibin to mature inhibin from the desired species.

Porcine and human ovarian cDNA libraries initially were probed for DNA encoding inhibin sequences using labelled oligonucleotides whose sequence was based on the partial amino acid sequence determined from analysis of purified porcine inhibin or, in the case of human cDNA, porcine cDNA probes. However, once having described cDNA encoding human and porcine inhibin and prodomains, one skilled in the art would realize that precisely hybridizing probes can be prepared from the described sequences in order to readily obtain the remainder of the desired human or porcine gene.

Nucleotide sequence analyses of identified porcine and human cDNA clones revealed the structures of the biosynthetic precursors of both forms of inhibin. Interestingly, the two inhibin chains are not derived from a single processed precursor. Instead, the two chains are translated from separate mRNAs and then assembled into the disulfide crosslinked two-chain molecule.

FIGS. 1B and 2B and 6, 8 and 9 depict the DNA encoding the polypeptide chains constituting porcine and human preproinhibin and preproactivin. Obviously, degenerate codons may be substituted for those disclosed in these figures where the same amino acid is encoded. The DNA of FIGS. 1B, 2B, 6, 8 and 9 is mutated in order to encode the amino acid variants of the α and β chains described above. In particular, the prepro sequences are deleted and a start codon is inserted immediately 5' to the mature chain in question so that the chain is expressed directly in recombinant culture. The DNA also is labelled, e.g. with radioactive phosphorous, and used to screen ovarian cDNA libraries from other species to identify α or β chain encoding DNA from such other species as is generally described above.

Covalent labelling of this DNA is accomplished with a detectable substance such as a fluorescent group, a radioactive atom or a chemiluminescent group by methods known per se. The labelled DNA is then used in conventional hybridization assays. Such assays are employed in identifying vectors and transformants as described in the examples infra, or for in vitro diagnosis such as detection of mRNA in tissues.

Lengthy sequences desirably are synthesized in host cells transformed with vectors containing DNA encoding them, e.g. inhibin or prodomain sequence. Vectors are used to amplify the DNA which encodes the chains, either in order to prepare quantities of DNA for further processing (cloning vectors) or for expression of the chains (expression vectors). An expression vector is a replicable DNA construct in which a DNA sequence encoding an α or β chain is operably linked to suitable control sequences capable of effecting their expression in a suitable host. Cloning vectors need not contain expression control sequences. Such control sequences include a transcriptional promoter, an optional operator sequence to control transcription, a sequence encoding suitable mRNA ribosomal binding sites (for prokaryotic expression), and sequences which control termination of transcription and translation. The vector should include a selection gene to facilitate the stable expression of the desired polypeptide and/or to identify transformants. However, the selection gene for maintaining α and/or β chain expression can be supplied by a separate vector in cotransformation systems using eukaryotic host cells.

Vectors comprise plasmids, viruses (including phage), and integratable DNA fragments i.e., fragments that are integratable into the host genome by recombination. The vectors described herein for use in eukaryotic cell expression of inhibin α and/or β chains contain plasmid sequences for cloning in microbes, where the plasmid replicates autonomously from the host genome, but the DNA is believed to integrate into the eukaryotic host cell genome upon transformation. Similarly, bacillus vectors that genomically integrate by homologous recombination in bacillus also are useful. However, all other forms of vectors which serve an equivalent function and which are, or become, known in the art are suitable for use herein.

Suitable vectors generally will contain replicon (origins of replication, for use in non-integrative vectors) and control sequences which are derived from species compatible with the intended expression host. Transformed host cells are cells which have been transformed or transfected with vectors containing inhibin α and/or β chain encoding DNA. Transformed host cells contain cloned DNA and, when transformed with an expression vector, also express the α and/or β chains. The expressed polypeptides will be deposited intracellularly or secreted into either the periplasmic space or the culture supernatant, depending upon the host cell selected and the presence of suitable processing signals in the expressed protein, e.g. homologous or heterologous signal sequences.

DNA regions are operably linked when they are functionally related to each other. For example, DNA for a presequence or secretory leader is operably linked to DNA for a polypeptide if it is expressed as a preprotein which participates in the secretion of the polypeptide; a promoter is operably linked to a coding sequence if it controls the transcription of the sequence; or a ribosome binding site is operably linked to a coding sequence if it is positioned so as to permit translation. Generally, operably linked means that the DNA sequences being linked are contiguous and, in the case of secretory leaders, contiguous and in reading phase.

Suitable host cells are prokaryotes, yeast or higher eukaryotic cells. Prokaryotes include gram negative or gram positive organisms, for example *E. coli* or Bacilli. Higher eukaryotic cells include established cell lines of mammalian origin as described below. A preferred host cell is *E. coli* 294 (ATCC 31,446) although other prokaryotes such as *E. coli* B, *E. coli* X1776 (ATCC 31,537), *E. coli* W3110 (ATCC 27,325), pseudomonas species, or *Serratia marcesans* are suitable.

Expression vectors for host cells ordinarily include an origin of replication (where extrachromosomal amplification is desired, as in cloning, the origin will be a bacterial origin), a promoter located upstream from the inhibin coding sequences, together with a ribosome binding site (the ribosome binding or Shine-Dalgarno sequence is only needed for prokaryotic expression), RNA splice site (if the inhibin DNA contains genomic DNA containing one or more introns), a polyadenylation site, and a transcriptional termination sequence. As noted, the skilled artisan will appreciate that certain of these sequences are not required for expression in certain hosts. An expression vector for use with microbes need only contain an origin of replication recognized by the intended host, a promoter which will function in the host and a phenotypic selection gene, for example a gene encoding proteins conferring antibiotic resistance or supplying an auxotrophic requirement. Inhibin DNA is typically cloned in *E. coli* using pBR322, a plasmid derived from an *E. coli* species (Bolivar, et al., 1977, "Gene" 2:95). pBR322 contains genes for ampicillin and tetracycline resistance and thus provides easy means for identifying transformed cells.

Expression vectors, unlike cloning vectors, must contain a promoter which is recognized by the host organism. This is generally a promoter homologous to the intended host. Promoters most commonly used in recombinant DNA constructions include the β-lactamase (penicillinase) and lactose promoter systems (Chang et al., 1978, "Nature", 275: 615; and Goeddel et al., 1979, "Nature" 281: 544), a tryptophan (trp) promoter system (Goeddel et al., 1980, "Nucleic Acids Res." 8: 4057 and EPO Appl. Publ. No. 36,776) and the tac promoter [H. De Boer et al., 1983, "Proc. Nat'l. Acad. Sci. U.S.A." 80: 21–25]. While these are the most commonly used, other known microbial promoters are suitable. Details concerning their nucleotide sequences have been published, enabling a skilled worker operably to ligate them to DNA encoding inhibin in plasmid vectors (Siebenlist et al., 1980, "Cell" 20: 269) and the DNA encoding inhibin or its derivative. Promoters for use in prokaryotic expression systems also will contain a Shine-Dalgarno (S.D.) sequence operably linked to the DNA encoding the inhibin, i.e., the S.D. sequence is positioned so as to facilitate translation. Generally, this means that the promoter and S.D. sequences located upstream from the second codon of a bacterial structural gene are substituted for the sequences of prepro inhibin located 5' to the mature α and/or β chains.

In addition to prokaryotes, eukaryotic microbes such as yeast cultures are transformed with inhibin-encoding vectors. *Saccharomyces cerevisiae*, or common baker's yeast, is the most commonly used among lower eukaryotic host microorganisms. However, a number of other strains are commonly available and useful herein. Yeast vectors generally will contain an origin of replication from the 2 micron yeast plasmid or an autonomously replicating sequence (ARS), a promoter, DNA encoding the α and/or β chain, sequences for polyadenylation and transcription termination, and a selection gene. A suitable plasmid for expression in yeast is YRp7, (Stinchcomb et al., 1979, "Nature", 282: 39; Kingsman et al., 1979, "Gene", 7: 141; Tschemper et al., 1980, "Gene", 10:157). This plasmid already contains the trpl gene which provides a selection marker for a mutant strain of yeast lacking the ability to grow in tryptophan, for example ATCC No. 44076 or PEP4-1 (Jones, 1977, "Genetics", 85: 12). The presence of the trpl lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., 1980, "J. Biol. Chem.", 255: 2073) or other glycolytic enzymes (Hess et al., 1968, "J. Adv. Enzyme Reg.", 7: 149; and Holland et al., 1978, "Biochemistry", 17: 4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EP 73,657A.

Other yeast promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes are also ligated into the expression vector 3' of the inhibin or derivative coding sequences to provide termination and polyadenylation of the mRNA.

Cultures of cells derived from multicellular organisms are the preferred host cells herein because it is believed that expression of hormonally active inhibin or activin will only occur in such cells, with microbial expression resulting at most only in immunological cross-reactivity. In principle, any higher eukaryotic cell culture is workable, whether from vertebrate or invertebrate culture. Propagation of vertebrate cells in culture per se has become a routine procedure in recent years [*Tissue Culture*, Academic Press, Kruse and Patterson, editors (1973)].

Suitable host cells for expressing $\alpha$ or $\beta$ chains in higher eukaryotes include: monkey kidney CVI line transformed by SV40 (COS-7, ATCC CRL 1651); baby hamster kidney cells (BHK, ATCC CRL 10); Chinese hamster ovary-cells-DHFR (described by Urlaub and Chasin, PNAS (USA) 77: 4216, [1980]); mouse sertoli cells (TM4, Mather, J. P., Biol. Reprod. 23: 243-251 [1980]); monkey kidney cells (CVI ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060652, ATCC CCL 51); rat hepatoma cells (HTC, M1, 54, Baumann, M., et al., J. Cell. Biol. 85: 1-8 [1980]) and TRI cells (Mather, J. P. et al., Annals N.Y. Acad. Sci. 383: 44-68 [1982]).

The transcriptional and translation control sequences in vertebrate cell expression vectors preferably are provided from viral sources. For example, commonly used promoters are derived from polyoma, Adenovirus 2, and most preferably Simian Virus 40 (SV40). The early and late promoters of SV40 are particularly useful because both are obtained easily from the virus as a fragment which also contains the SV40 viral origin of replication (Fiers et al., 1978, "Nature", 273: 113). Smaller or larger SV40 fragments may also be used, provided the approximately 250 bp sequence extending from the Hind III site toward the Bgl I site located in the viral origin of replication is included. Further, it is also possible to utilize the genomic promoters, control and/or signal sequences normally associated with the $\alpha$ or $\beta$-chains, provided such control sequences are compatible with and recognized by the host cell.

An origin of replication may be provided either by construction of the vector to include an exogenous origin, such as may be obtained from SV40 or other viral (e.g. Polyoma, Adenovirus, VSV, or BFV) source, or may be provided by the host cell chromosomal replication mechanism. If the vector is integrated into the host cell chromosome, the latter is often sufficient.

Rather than using vectors which contain viral origins of replication, mammalian cells are cotransformed with DNA encoding a selectable marker and DNA encoding the $\alpha$ and/or $\beta$ chains. An example of a suitable selectable marker is dihydrofolate reductase (DHFR) or thymidine kinase. Such markers are proteins, generally enzymes that enable the identification of transformant cells, i.e., cells which had been competent to take up exogenous DNA. Generally, identification is by survival of transformants in culture medium that is toxic to untransformed cells or from which the cells cannot obtain a critical nutrient without having taken up the marker protein.

In selecting a preferred host mammalian cell for transfection by vectors which comprise DNA sequences encoding both inhibin and DHFR, it is appropriate to select the host according to the type of DHFR protein employed. If wild type DHFR protein is employed, it is preferable to select a host cell which is deficient in DHFR thus permitting the use of the DHFR coding sequence as a marker for successful transfection in selective medium which lacks hypoxanthine, glycine, and thymidine (hgt−). An appropriate host cell in this case is the Chinese hamster ovary (CHO) cell line deficient in DHFR activity, prepared and propagated as described by Urlaub and Chasin, 1980, "Proc. Nat'l. Acad. Sci." (USA) 77: 4216.

On the other hand, if DNA encoding DHFR protein with low binding affinity for methotrexate (MTX) is used as the controlling sequence, it is not necessary to use DHFR resistant cells. Because the mutant DHFR is resistant to MTX, MTX containing media can be used as a means of selection provided that the host cells are themselves MTX sensitive. Most eukaryotic cells which are capable of absorbing MTX appear to be methotrexate sensitive. One such useful cell line is a CHO line, CHO-K1 (ATCC No. CCL 61). Preferably, transformants are first selected for neomycin resistance (the transfection is conducted together with DNA encoding the neomycin resistance gene), followed by MTX amplification of the $\alpha$ and/or $\beta$ chain expression as the case may be. See Kim et al., "Cell" 42: 129-138 (1985) and EP 160,457A.

Other methods suitable for adaptation to the synthesis of $\alpha$ and/or $\beta$ chains in recombinant vertebrate cell culture are described in M-J. Gething et al., "Nature" 293: 620-625 (1981); N. Mantei et al., "Nature" 281: 40-46; and A. Levinson et al., EP 117,060A and 117,058A.

The inhibin $\alpha$ chain is expressed in recombinant cell culture with or without either of the $\beta$-chain molecules. Similarly, host cells are transformed with DNA encoding either or both of the mature β-chains. Based on analogy to TGF-β, the mature β-chains are capable of forming homodimers or $\beta_A/\beta_B$ heterodimers upon expression in recombinant culture. These structures are not inhibin and will be referred to herein as β-chain dimers or activin. These are useful in the preparation of active inhibin, serving as sources of the β-chain, or are used as gel electrophoresis standards to detect the diversion into β-chain dimers of β-chains synthesized in α and β chain cotransformants. As will be seen in Example 4, this is not a hypoehetical problem. Of course, the dimers also are useful in modulating reproduction as noted above.

β-chain hetero-or homodimers are separated by in vitro unfolding of the individual chains followed by oxidative disulfide bond formation with the α-chain in accord with processes generally known per se. Preferably, however, in preparing mature inhibin the recombinant host is transformed with DNA encoding both the α and either of the β-chains. The intact hormonally active molecule is then assembled by the host cell in vivo, and it is thus unnecessary to combine the two chains by in vitro processing. The DNA encoding the α and β-chains is preferably located on the same vector, and under the control of the same promoter, but this is not essential.

Certain β-chain amino acid sequence variants identified in the screening procedure will not bind to pituitary cell surface receptors nor as a consequence will they exhibit hormonal activity. Such variants, when expressed as homodimers in recombinant cell culture, are useful in immunoassays for activin when they bear immunological epitopes cross-reactive with the native β-chain. In addition, such variants are coexpressed with DNA encoding hormonally active β-chain to yield a hybrid bearing native and variant β-chain. In this case the variant serves to stabilize the structure of the native β-chain. This form of β-chain heterodimer is useful, like the homodimer, in immunoassays for activin. It also may function as an activin antagonist.

The activin/inhibin β-chains also are coexpressed with TGF-β in order to produce β-chain/TGF-β hybrids. Vectors and methods for the expression of TGF-β are known. For example, see Deryncle et al., Human Transforming Growth Factor-β Complementary DNA Sequence and Expression in Normal and Transformed Cells "Nature" 316: 701–705 (1985). Cotransformation of mammalian host cells by vectors bearing the TGF-β gene as described by Derynck et al. together with the $\beta_A$ or $\beta_B$ chains of activin/inhibin will result in secretion of a proportion of β-chain/TGF-β hybrid dimers. This hybrid is useful in preparing TGF-β/β-chain immunogens or in immunoassays.

Inhibin, activin or prodomain sequences are recovered from transformed cells in accord with per se known procedures. When a polypeptide is expressed in recombinant bacteria as a refractile body, the desired polypeptide is recovered and refolded by conventional methods. Alternatively, the culture supernatants from transformed cells that secrete activin or inhibin, preferably mammalian cells, are simply separated from the cells by centrifugation. Then the inhibin generally is purified by successive purification procedures that include heparin-Sepharose affinity chromatography, gel filtration and at least one and preferably several RP-HPLC (reverse phase high pressure liquid chromatography) steps using different conditions in the stationary phase and/or mobile phase. Prodomain sequences produced by in vitro synthesis will be purified by conventional methods.

The prodomain polypeptides that are preferred for use herein are recovered from the culture media of recombinant cells transformed to synthesize the α and/or β chains as appropriate for the desired prodomain. Specifically, they are recovered by separating the culture medium polypeptides on native electrophoresis gel, excising bands having the predicted molecular weight and thereafter purifying the eluted polypeptides further, for example by FPLC or HPLC, followed by amino acid sequence determination for the substantially homogeneous separated polypeptides. Purified prodomain polypeptides then are used to raise antibodies, e.g., in rabbits, which when used in immunoaffinity purification will simplify the recovery of the prodomains.

In the preferred procedure for isolating porcine hormonally active inhibin, clarified transformant culture supernatant or cell lysate is first purified by heparin-Sepharose affinity chromatography, next by gel filtration on Sephacryl S-200 gel and then with four successive RP-HPLCs using different mobile phase gradients and/or derivatized silica supports. Preferably, stationary phases having relatively low hydrophobicity are used, with C3–C8 columns being preferred and C3–C5 and phenyl columns being particularly preferred. Solute specificity of the mobile phase is preferably adjusted by varying the concentration of an organic component, particularly acetonitrile. Although a single RP-HPLC fractionation significantly increases the purity relative to the gel-filtrated material, two or more, and preferably four, RP-HPLC purifications are generally performed subsequent to successive treatment by heparin-Sepharose chromatography and gel filtration. This method has been found to be adaptable to the purification of human inhibin from recombinant cell culture as well.

The first step of the purification is heparin-Sepharose affinity chromatography, in which the protein is adsorbed to the Sepharose-bound heparin moieties under application conditions, and the adsorbed inhibin material is recovered by 1M NaCl elution. This step greatly expedites the purification procedure for crude extracts because it allows a relatively large volume of a crude extract to be processed fairly rapidly while recovering an amount of protein exhibiting total inhibin activity equal to at least 90% of that of the crude extract.

For the detection of inhibin activity in the various column fractions, aliquots ranging from 0.01% to 0.1% by volume are removed, and after adding 100 μg human serum albumin in 100 μl water, the solvents were evaporated in a Speed-Vac concentrator (Savant, Hicksville, N.Y.). The residue was redissolved in 3 ml 1% fetal bovine serum in HDHEM, filtered through a Millex-GS 0.22 μm filter (Millipore Corp., Bedford, Mass.) and assayed in duplicate. To speed up the bioassays during the purification process, only basal inhibition of FSH secretion exerted by the inhibin activity is determined and plotted in the region where the inhibin proteins were expected to migrate in the chromatograms.

To perform the heparin-Sepharose affinity chromatography, cell debris is spun down in a Beckman J2-21 centrifuge (Beckman Instruments, Inc., Palo Alto, Calif.) using a JA-20 rotor at 10,000 rpm for 30 minutes. One half of the supernatant is diluted to 10 times its volume by the addition of 0.01M Tris-HCl containing 0.1M NaCl, pH 7, in an Erlenmeyer flask and pumped simultaneously via silastic tubes (0.76 mm ID) into heparin-Sepharose (Pharmacia Fine Chemicals, Piscataway, N.J.) columns (3.5×9 cm) by two Rabbit 4-channel peristaltic pumps (Rainin Instrument Co., Inc., Emeryville, Calif.) at 40 ml/hr per column. After all the fluid has been pumped through the heparin-Sepharose, the eight columns are washed simultaneously with 0.01M Tris-HCl, pH 7, containing 0.1M NaCl in the same manner. The adsorbed proteins with inhibin activity are removed by washing the eight columns simultaneously with 0.01M Tris-HCl containing 1M NaCl, pH 7, as above, and the wash is collected into fractions. The inhibin activity is monitored by the in vitro bioassay described above. The columns are regenerated by further washing with 2M NaCl in 0.01M Tris-HCl, pH 7, and re-equilibrated with 0.01M Tris-HCl containing 0.1M NaCl for purification of remaining extract.

Next, the material is fractionated by gel filtration to separate proteins generally according to their molecular weights. The fractions having inhibin activity extracted by the heparin-Sepharose columns are pooled and dialyzed overnight to remove NaCl in a 28.6 mm cylinder diameter Spectrapor No. 3 membrane tubing with $M_r$ cutoff at 3,500 (Spectrum Medical Industries, Inc., Los Angeles, Calif.) against 30% acetic acid. The retained fluid is centrifuged, as above, to remove a white precipitate, and the supernatant is divided into equal portions for applying to 5×100 cm Sephacryl S-200 superfine columns (Pharmacia Fine Chemicals, Piscataway, N.J.). Each column is eluted with 30% acetic acid at 20 ml for 22 min., and the column fractions are monitored by UV absorption at 280 nm and by bioassay.

The bioassay-positive protein from the S-200 columns is pooled and lyophilized. The lyophilized material is dissolved in 0.2N acetic acid (1 ml/ml) and filtered through a Millex-HA 0.45 μm filter (Millipore Corp., Bedford, Mass.). The filtrate is applied directly onto a 1×25 cm Vydac 5-μm particle-size C4 column (The Separations Group Hesperia, Calif.) and developed with a gradient of TEAP buffer. In the TEAP system, buffer A consists of 0.25N triethylammonium phosphate pH 3, and buffer B is 80% acetonitrile in buffer A. After all the filtrate had been loaded, the column is washed with the aqueous buffer A until the UV absorption reached baseline. The fractions exhibiting inhibin activity are separated in a Beckman 332 gradient liquid chromatography system (Beckman Instruments, Inc., Berkeley, Calif.) equipped with a Spectroflow 757 UV detector (Kratos Analytical Instruments, Ramsey, N.J.), a Soltec 220 recorder (Soltec Corp., Sun Valley, Calif.) and a Redirac 2112 fraction collector (LKB Instruments, Inc., Gathersburg, Md.). Zones of inhibin activity are detected by bioassay.

Inhibin protein containing the $\beta_B$ chain is further purified free of inhibin containing the $\beta_A$ species, if desired, by two more RP-HPLC steps. The first step uses a 1×25 cm Vydac 5-μm-particle-size C4 column and a trifluoroacetic acid (TFA) buffer system and the second step employs a 1×25 cm Vydac 5-μm-particle-size Phenyl column and the TEAP buffer system. In the TFA system, buffer A contains 1 ml trifluoroacetic acid in 999 ml water and buffer B is 1 ml trifluoroacetic acid in 199 ml water and 800 ml acetonitrile. The two inhibin species elute separately. Inhibin accumulated from a few batches was concentrated by RP-HPLC using a 0.46×25 cm Aquapore RF-300 10 μm-particle-size column (Brownlee Labs., Santa Clara, Calif.) and the TFA buffer system. Ordinarily, however, this purification step will not be used with cell culture supernatants from transformants with DNA encoding only the $\beta_A$ or $\beta_B$ chains.

Inhibin, activin, prodomain sequences or their variants are administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. Intravenous administration in isotonic saline, phosphate buffer solutions or the like is suitable.

The polypeptide herein should be administered under the guidance of a physician, and pharmaceutical compositions will usually contain an effective amount of the peptide in conjunction with a conventional, pharmaceutically-acceptable carrier. The dosage will vary depending upon the specific purpose for which the protein is being administered, and dosage levels in the range of about 0.1 to about 1 milligram per Kg. of body weight may be used when inhibin is administered on a regular basis as a male contraceptive.

Inhibin, activin, prodomain sequences or their variants desirably are administered from an implantable or skin-adhesive sustained-release article. Examples of suitable systems include copolymers of L-glutamic acid and gamma ethyl-L-glutamate (U. Sidman et al., 1983, "Biopolymers" 22(1): 547–556), poly (2-hydroxyethyl-methacrylate) (R. Langer et al., 1981, "J. Biomed. Mater. Res." 15: 167–277 and R. Langer, 1982, "Chem. Tech." 12: 98–105), ethylene vinyl acetate (R. Langer et al., Id.), or poly-D-(−)-3-hydroxybutyric acid (EP 133,988A). Such articles are implanted subcutaneously or are placed into contact with the skin or mucous membranes.

In order to simplify the Examples certain frequently occurring methods will be reference by shorthand phrases.

Plasmids are designated by a low case p preceded and/or followed by capital letters and/or numbers. The starting plasmids herein are commercially available, are publicly available on an unrestricted basis, or can be constructed from publicly available plasmids or DNA in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate. The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, about 1 μg of plasmid or DNA fragment is used with about 1 unit of enzyme in about 20 μl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, Molecular Cloning pp. 133-134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9: 6103-6114, and D. Goeddel et al., 1980, "Nucleic Acids Res." 8: 4057.

"Southern Analysis" is a method by which the presence of DNA sequences in a digest or DNA-containing composition is confirmed by hybridization to a known, labelled oligonucleotide or DNA fragment. For the purposes herein, unless otherwise provided, Southern analysis shall mean separation of digests on 1 percent agarose, denaturation and transfer to nitrocellulose by the method of E. Southern, 1975, "J. Mol. Biol." 98: 503-517, and hybridization as described by T. Maniatis et al., 1978, "Cell" 15: 687-701.

"Transformation" means introducing DNA into an organism so that the DNA is replicable, either as an extrachromosomal element or chromosomal integrant. Unless otherwise provided, the method used herein for transformation of *E. coli* is the CaCl$_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

"Preparation" of DNA from transformants means isolating plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All citations are expressly incorporated by reference.

EXAMPLE 1

Isolation Of Cloned Inhibin α-Subunit cDNAs

The strategy for identification of clones containing coding sequences for the porcine inhibin subunits was based on the "long-probe" approach, successful in some previous instances (Anderson et al., 1983, "Proc. Nat. Acad. Sci. USA" 80: 6836-6842 and Ullrich et al., 1984, "Nature" 309:418-425). Briefly, a high-complexity cDNA library constructed in λgt10 and derived from porcine ovarian mRNA by oligo-dT-primed cDNA synthesis was screened with a single 64-base-long synthetic oligodeoxynucleotide directed against the N-terminal amino acid sequence of the α-chain of porcine inhibin. It was found that the library is to be prepared from fresh ovarian tissue because the inhibin chain mRNA was apparently quite labile. Approximately 1 in 2,000 plaques hybridized with this probe, and sequence analysis of several hybridizing cloned cDNAs confirmed correct probe identification. This analysis revealed that none of the characterized cDNAs contained sufficient sequence information to predict the complete structure of the α-chain precursor protein. Rather than analyzing more clones from the same cDNA library, a second library was constructed by 3' extension on ovarian mRNA of a synthetic oligodeoxynucleotide complementary to a sequenced region encoding α precursor residues 60–64 (FIG. 1A). This library was screened with a suitable restriction fragment from a previously analyzed cDNA and yielded several isolates which specified the remainder of the DNA sequences encoding the N-terminal region of the α precursor. Completeness of the coding sequence was judged from the presence of a long reading frame which specifies the porcine α-chain peptide sequence and starts with a methionine codon preceded by an in-frame stop codon and followed by a hydrophobic sequence bearing the hallmarks of a signal peptide. The full sequences for the precursor protein and its cDNA are shown in FIG. 1B. The complete protein including signal peptide has an Mr of ~40K consisting of 364 amino acids, of which the C-terminal 134 ($M_r$~14.5K) constitute the porcine inhibin α-chain. There are several Arg-Arg sequences in the proregion of the precursor, one of them directly preceding the α subunit. We believe that this latter pair of basic residues is the processing site for the proteolytic release of the α peptide. The deduced precursor sequence predicts two N-linked glycosylation sites, one within the α chain proper.

In addition to the coding region, the cDNA sequence contains a 3'-untranslated sequence of 167 nucleotides, including the canonical AATAAA polyadenylation signal, and a 5'-untranslated region, the proper length of which is presently unknown.

The detailed method was as follows:

Polyadenylated mRNA was prepared from freshly frozen porcine ovaries (Kaplan et al., "J. Biochem." 183: 181-184). An oligo-dT-primed cDNA library of ~6×10⁶ clones in λgt10 (Huynh et al., 1984, DNA Cloning Techniques, Ed. D. Clover) was prepared from 5 μg polyA+ mRNA as described by Wood et al., "Nature" 312: 330-337 (1984), except that the EcoRI adaptors used had the sequence

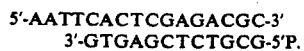

Approximately 1×10⁶ unamplified cDNA clones were screened with 5 α-subunit oligonucleotide 5'-ACCGCCCCTTTGCCTTGGCCTTGGTCCCCTG-CTGCTCTGAGACTGCTGCAGAGACCTCCT-GAGG-3', based on the amino acid sequence underlined in FIG. 1B. Hybridization was carried out with the phosphorylated ³²P-labelled probe in 5×SSC, 40% formamide at 37° C. Filters were washed at 50° C. with 1×SSC, 0.1% SDS. Approximately 500 hybridization positive clones were obtained, twelve of which were purified and examined for insert size. The EcoRI inserts of five of these (λPIN-α2, -α5, -α5, -α9, -α10) were subcloned into M13 derivatives (Messing et al., 1981 "Nucl. Acids Res." 9: 309-321) and sequenced by the dideoxy chain termination method of Sanger et al., "Proc. Nat. Acad. Sci. USA" 74:5463-5467 (1977). A specifically primed library was prepared by priming 5 μg of polyA+ mRNA with the oligonucleotide 5'-CCCCACAGCATGTCTT-3' (complementary to nucleotides 248-263) and subsequent cloning into λgt10. Approximately $2 \times 10^5$ clones of the $1 \times 10^6$ clones obtained were screened with the 5' 100 bp EcoRI-BamHI fragment prepared from λPIN-α2. Twelve of the 170 hybridization positive clones obtained were purified and two (λPIN-S12s, -S4s) were sequenced by the dideoxy method. The complete nucleotide sequences of the α-subunit cDNAs were obtained by subcloning various restriction fragments from the different λ isolates into the M13 phage derivatives. Compressions were resolved by the use of deoxyinosine mixes in combination with the E. coli single stranded binding protein (Pharmacia).

Isolation of Cloned Inhibin β Subunit cDNAS

Figure 2A:
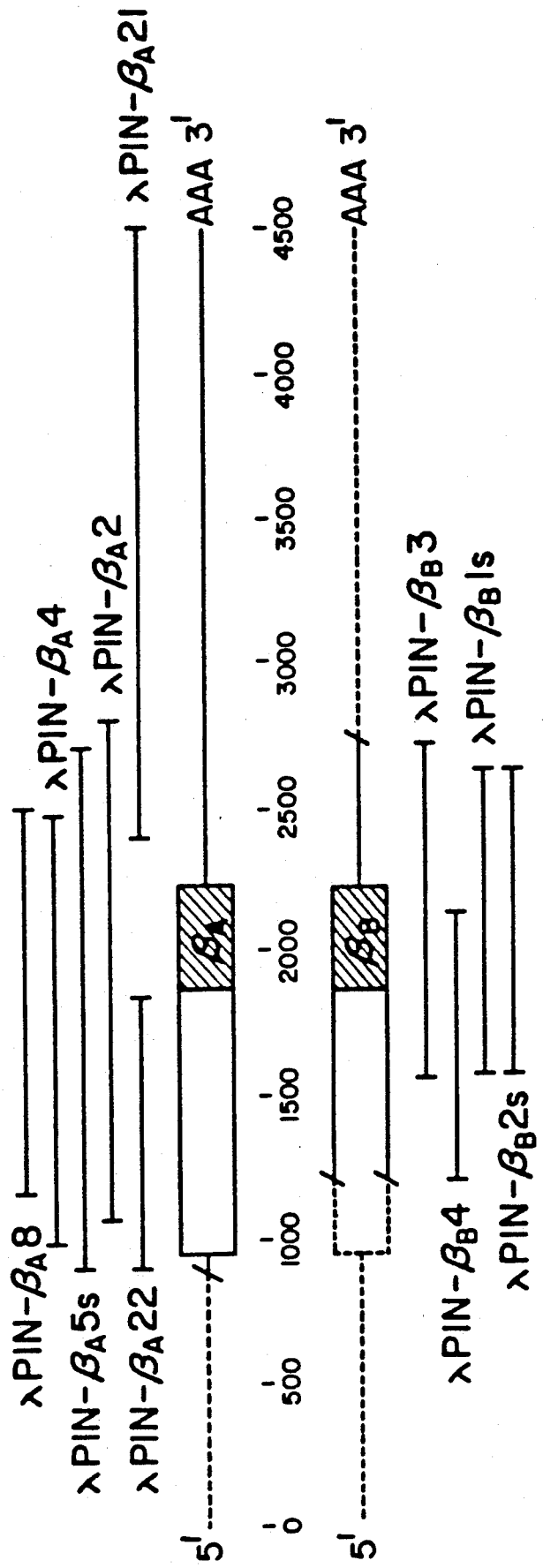
FIG. 2A is a schematic representation of the porcine $β_A$ and $β_B$ subunit mRNAs with coding sequences boxed. The $β_A$ and $β_B$ subunits (dashed) are encoded towards the 3' end of the coding sequences. The 3' and 5' untranslated regions are shown as a line. The length of the 5' and 3' untranslated region of the βB subunit mRNA is inferred from the size of the mRNA (FIG. 3) and its obvious similarity to the $β_A$ mRNA. Tentative regions of the cDNAs are shown as dashes in the diagram. The relative positions of the overlapping oligo-dT primed cDNA clones and the randomly primed clones (λPIN$β_A$5s, λPIN$β_B$1s, and λPIN$β_B$2s) are indicated. The scale is in nucleotides from the 5' end of the 4.5 kb mRNA.

The cDNA sequences encoding the precursors of the inhibin β subunits were obtained from the same cDNA libraries used for the α subunit. Overlapping cDNA clones were isolated by screening first with single long synthetic oligodeoxynucleotide probes based on the two N-terminal β subunit sequences and subsequently with suitable restriction fragments derived from characterized cDNA clones which served as probes for "walking" in both 5' and 3' directions (FIG. 2A).

In more detail, approximately $2 \times 10^5$ oligo-dT primed ovarian cDNA clones were screened with the 5' end labelled $\beta_A$ oligonucleotide, 5'-AAGAAG-CAGTTCTTTGTGTCCTTCAAG-GACATTGGCTGGAATGACTGGATCATTGC-3' based on the amino acid sequence of residues 321-339. Five hybridization positives were obtained, of which three proved to contain $\beta_A$ coding sequences (λPIN-$\beta_A$2, -$\beta_A$4, -$\beta_A$8). A 5' end 154 bp EcoRI-HindIII (nucleotides 158-297) fragment and a 3' end 213 bp EcoRI-PST fragment (nucleotides 1679-1892) derived from λPIN$\beta_A$2 were used to screen $2 \times 10^6$ oligo-dT primed cDNA clones and $2 \times 10^5$ clones from the α-chain specifically primed library. Out of the sixteen clones analyzed in detail two were found to have longer 5' ends (λPIN-$\beta_A$5s, -$\beta_A$22) and one clone λPIN-$\beta_A$21 contained the entire 3'-untranslated region. Porcine inhibin $\beta_B$ subunit cDNA clones were isolated by screening $2 \times 10^5$ clones from the specifically primed library with the $\beta_B$ oligonucleotide 5'-GGCCTGGAGTGT-GATGGGAGAACCAACCTGTCCTGCCGCCAG-GAATTTTTCATCGATTTCAGGCT-3', which was based on the NH$_2$-terminal sequence described in FIG. 1A. Positive clones were further screened with the oligonucleotide inosine probe

("I" in this sequence stands for inosine), which covers all the possibilities in the non-coding strand for the amino acid sequence QQFFIDF. Two clones (λPIN$\beta_B$-1s, -2s) were isolated and sequenced and found to code for the $\beta_B$ subunit. A 230 bp EcoRI-Sma (nucleotides 21-251) fragment was isolated from λPIN$\beta_B$-I and used as a hybridization probe to screen $2 \times 10^6$ oligo-dT primed cDNA clones. Two positives were obtained (λPIN$\beta_B$-3,4). The nucleotide sequence of these overlapping clones was used to construct the sequence shown. All sequences were obtained by subcloning specific fragments into M13 phage vectors (Messing et al., op cit.). The EcoRI restriction sites referred to above are all contained within the cDNA adaptor fragment, and do not refer to sequences present in the cDNA.

We noted that only very few clones from the oligi-dT-primed library (4 out of $2 \times 10^5$) hybridized with the synthetic probe for the β-subunit of inhibin A. Although most of these proved correct by DNA sequence analysis, none contained a full 3'-untranslated region, as judged by the absence of a polyA homopolymer at their 3' ends. Absence of polyA tails suggested the existence of a very long 3'-untranslated sequence in this mRNA species and/or structural region(s) which prove difficult to copy by the polymerases used for library construction. Unexpectedly, a higher abundance (~10-fold) of inhibin $\beta_A$ subunit coding sequences was found in the cDNA library made by specific priming on α-subunit mRNA. This library was screened with the synthetic probe for the β-chain of inhibin A on the subsequently refuted theory that the α precursor mRNA might also encode the β subunit. The high abundance of inhibin $\beta_A$ cDNA in this library was later traced to fortuitous complementarity of the specific α chain primer to a region in the 3'-untranslated portion of the corresponding mRNA.

Only four cloned cDNAs encoding the β subunit of inhibin B were found in our libraries. The sequence information obtained from these clones failed to reveal the complete structure of the corresponding precursor protein and its cDNA. The sequence of cDNAs and deduced protein structures for the precursors of the β subunits are compared in FIG. 2B. The nucleotide sequence of inhibin $\beta_A$ subunit cDNA is 3.6 kb in length and contains an open reading frame for a protein of 425 amino acids (Mr~46K), the C-terminal 116 residues of which represent the β subunit proper (Mr~13K). This reading frame begins with a methionine codon followed by a sequence that codes for a characteristic signal peptide, the true length of which is believed to be 29 residues. The encoded β subunit is preceded by a string of 5 arginines at which it is presumably proteolytically cleaved from the precursor. Similar to the α subunit precursor, this β precursor contains several additional pairs of basic residues at which hitherto unknown biologically active peptide entities are believed to be released. It also contains one possible site for N-linked glycosylation in the proregion (Asn, residue 165).

The deduced protein sequence for the β subunit of inhibin B shows high homology with the $\beta_A$ subunit sequence. 71 amino acid residues are identical and most changes are conservative in nature. Sequence homology, although of a lesser degree, is also found in the proregion of both β subunit precursors. Interestingly, an extremely purine-rich sequence rerely seen in coding regions but present in the cDNA encoding the inhibin $\beta_A$ precursor and resulting in a curious amino acid sequence is not found in the cDNA which codes for the homologous $\beta_B$ precursor. This results in a gap of 22 amino acid residues from the $\beta_B$ precursor of inhibin when protein sequences are aligned for maximal homology. Such alignment also brings about a perfect match in the cysteine positions of both precursors (see FIG. 2B).

Northern Analysis of α and β chain Precursor mRNAs

Ovarian total and polyadenylated RNAs were analyzed by the Northern procedure using the sequenced cDNAs as probes to assess size and relative abundance of the mRNAs which encode the peptide subunits α and β and $\beta_B$ of the heterodimeric inhibin molecule. Polyadenylated mRNA (2 μg: lanes a, b, c, and f; 8 μg: lane d) and total RNA (10 μg: lanes e and g) were electrophoresed into a formaldehyde 1.2% agarose gel and blotted onto nitrocellulose filters. The following $^{32}$P-labelled cDNA fragments were used as hybridization probes under stringent conditions. Lane a: 240 bp EcoRI-SmaI (nucleotides 134–371) from α subunit cDNA; b: 154 pb EcoRI-HindIII (nucleotides 158–297) from $\beta_A$ subunit cDNA; c: 230 bp EcoRI-Sma (nucleotides 21–251) from $\beta_B$ subunit cDNA; d and e: EcoRI insert of λPIN-α2; f and g: EcoRI insert of λPIN-$\beta_A$5. Filters were washed for 2 hours with 3 changes of 0.1×SSC, 0.1% SDS at 60° C.

Analysis showed (FIG. 3) that α and β mRNAs are of different size and abundance, as indicated by results obtained from cDNA cloning. From their respective band intensities the α precursor mRNA is extimated to be at least of 10-fold higher abundance that the mRNA for the $\beta_A$ precursor, and approximately 20-fold higher than the mRNA for the $\beta_B$ precursor.

Figure 2B:
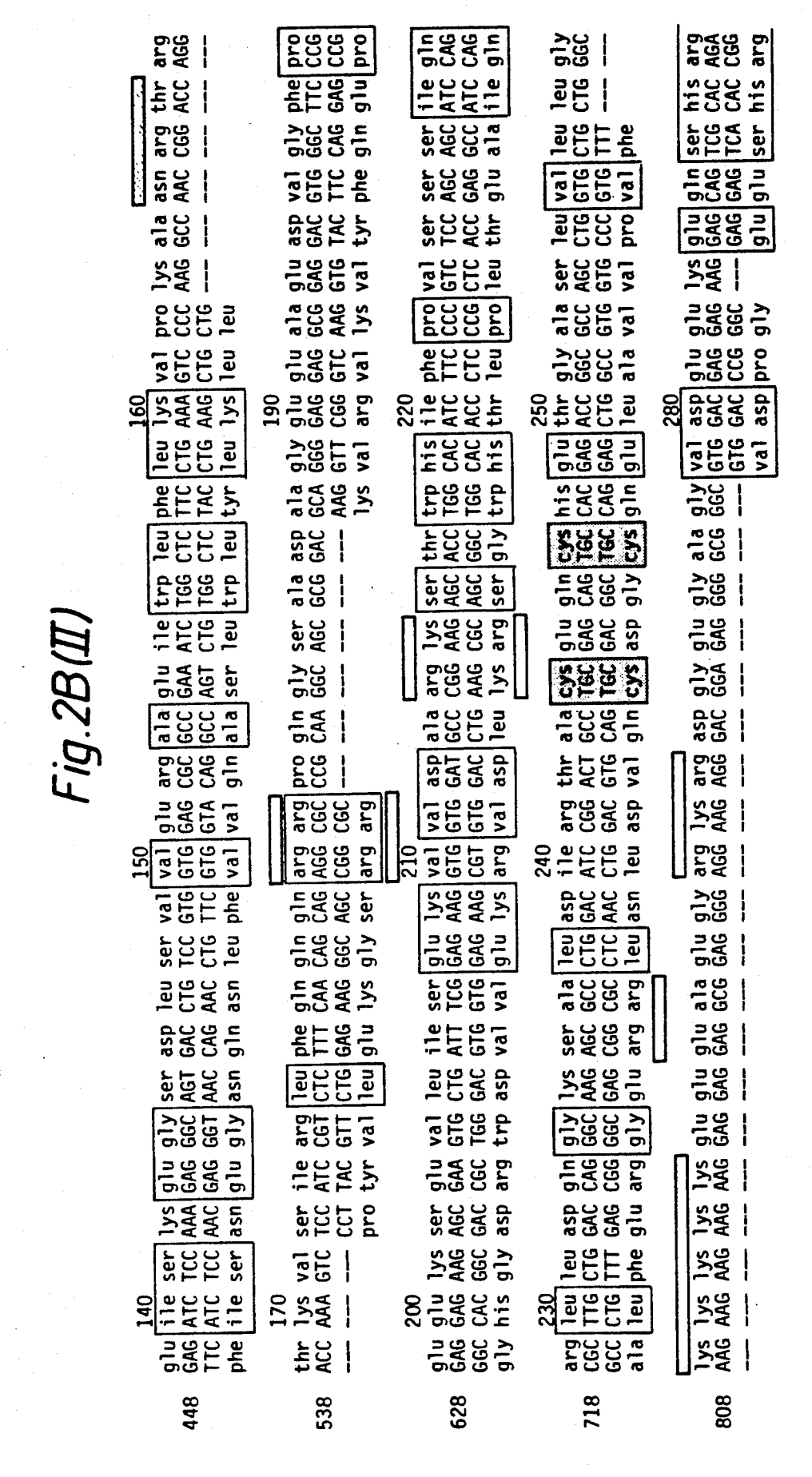
Figure 2B:
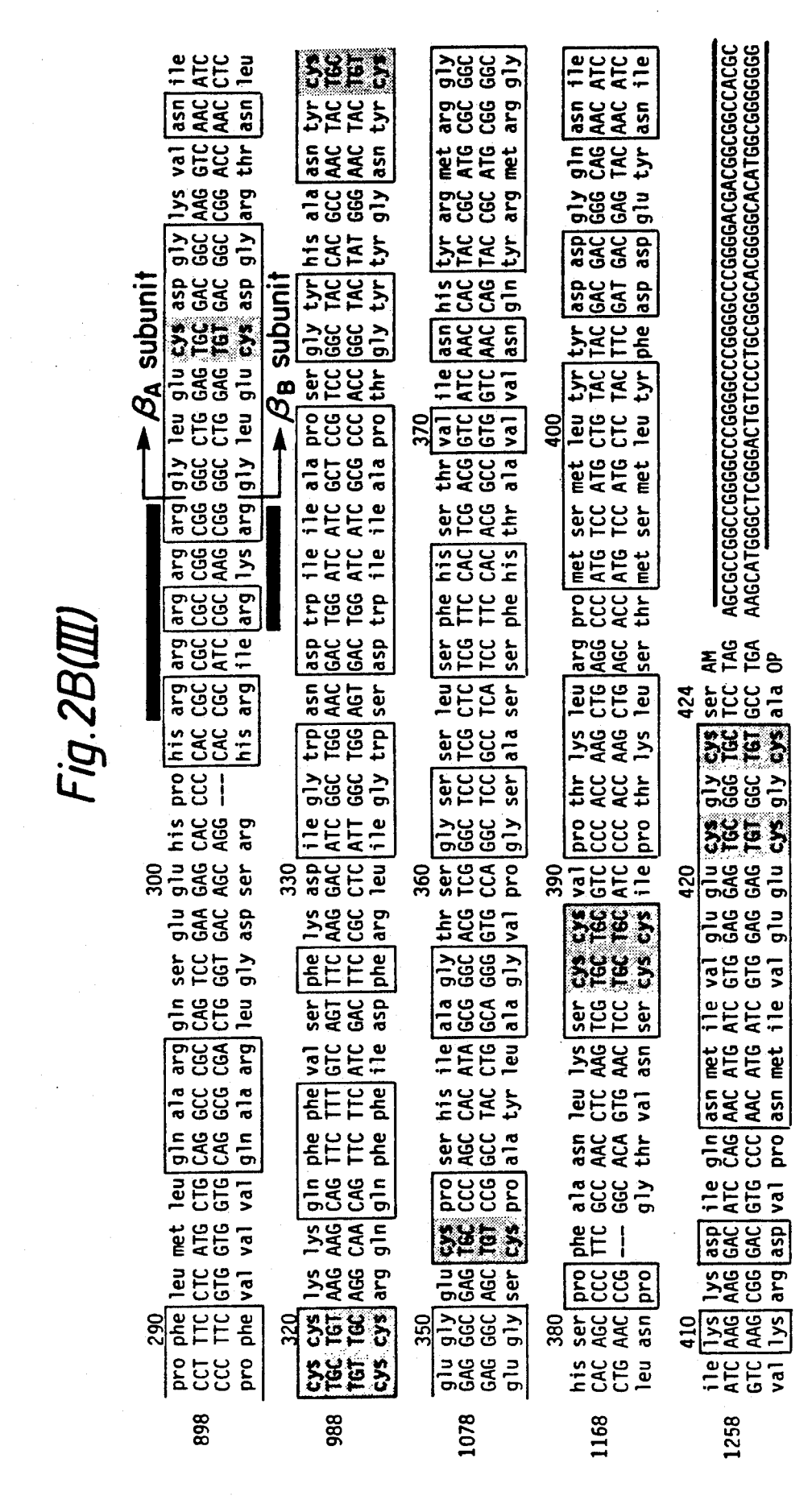

Using ribosomal RNAs as size standards, the α precursor mRNA, which is a single species, is ~1500 nucleotides in length, a size in good agreement with the cloned cDNA sequence (FIG. 1B). $\beta_A$ precursor mRNA sequences are represented by two main species of ~4.5 and ~7.2 kb in length. The relatively higher intensity of both species in polyadenylated than total RNA suggests that the 4.5 kb species does not represent 28S RNA which hybridized to the cDNA probe. Thus, the β precursor cDNA sequences shown in FIG. 2B are thought to represent the 4.5 kb mRNA, suggesting that the 5' untranslated region for the $\beta_A$ mRNA is approximately 900 nucleotides long. The $\beta_B$ precursor is encoded on one mRNA, of approximately 4.5 kb in size, which is present at roughly half the level of the two $\beta_A$ mRNAs. Since the two β mRNAs are closely related, one can predict that both mRNAs have a similar structure and thus the $\beta_B$ mRNA presumably possesses a long 5' and 3' untranslated region equivalent to that shown for the $\beta_A$ mRNA. Choice of a different polyadenylation signal might explain the existence of the 7.2 kb species.

Homology To Transforming Growth Factor-β

The mature α and β inhibin subunits contain seven and nine cysteine residues, respectively. Upon alignment of the cysteine residues it is apparent that the two subunits share a similar cysteine distribution and some sequence homology exists around these residues (FIG. 4), suggesting that both types of subunits derive from one ancestral gene. Suprisingly, significant homology was found between the β chain and the primary structure of human TGF-β recently determined. As outlined in FIG. 4, both peptides are of nearly equal length (inhibin $\beta_A$ subunit, 116; $\beta_B$ subunit 115; TGFS, 116 residues) and show a strikingly similar distribution of their nine cysteine residues. Using this cysteine "skeleton" for alignment, the $\beta_A$ and TGF-β sequences have an additional 31 residues in identical positions and show conservative changes in nine homologous places. Similar high homologies are seen upon comparison of the $\beta_B$ and β-TGF. Some gaps were introduced for better alignment (FIG. 4). The overall homology reaches 35%, but approaches 60% in certain sections (cf. porcine inhibin $\beta_A$ chain residues 11–45 and TGF residues 15–49), a very high degree of homology considering the difference in species. Interestingly, this homology extends beyond the termination codon for protein synthesis in the respective cDNAs. Thus, the cDNAs for TGF-β and both inhibin β subunits contain a highly G and C rich sequence in this region, and they also possess unusually long 5' and 3' untranslated regions.

One can discount the suggestion that the β subunit of inhibin is the porcine equivalent of human TGF-β, since there is almost absolute homology between human and murine β-TGFs. These findings strongly indicate that both inhibin subunits and TGF-β have a common ancestor and belong to one gene family. All three peptides are derived from similarly-sized precursors ($M_r$ ~40K) where they occupy the C-terminal 110 or so residues and are released by proteolytic cleavage at pairs of arginines. They form homo- or heterodimers, and subunits in the biologically active complex are linked by disulfide bridges. However, there is little sequence homology between TGF-β and the β subunits in the pro parts of their precursors, although the regions comprising the odd residues which precede the β subunit and TGF peptides display limited but significant sequence relatedness.

EXAMPLE 2

Recombinant Synthesis of Porcine Inhibin

Figure 5A:
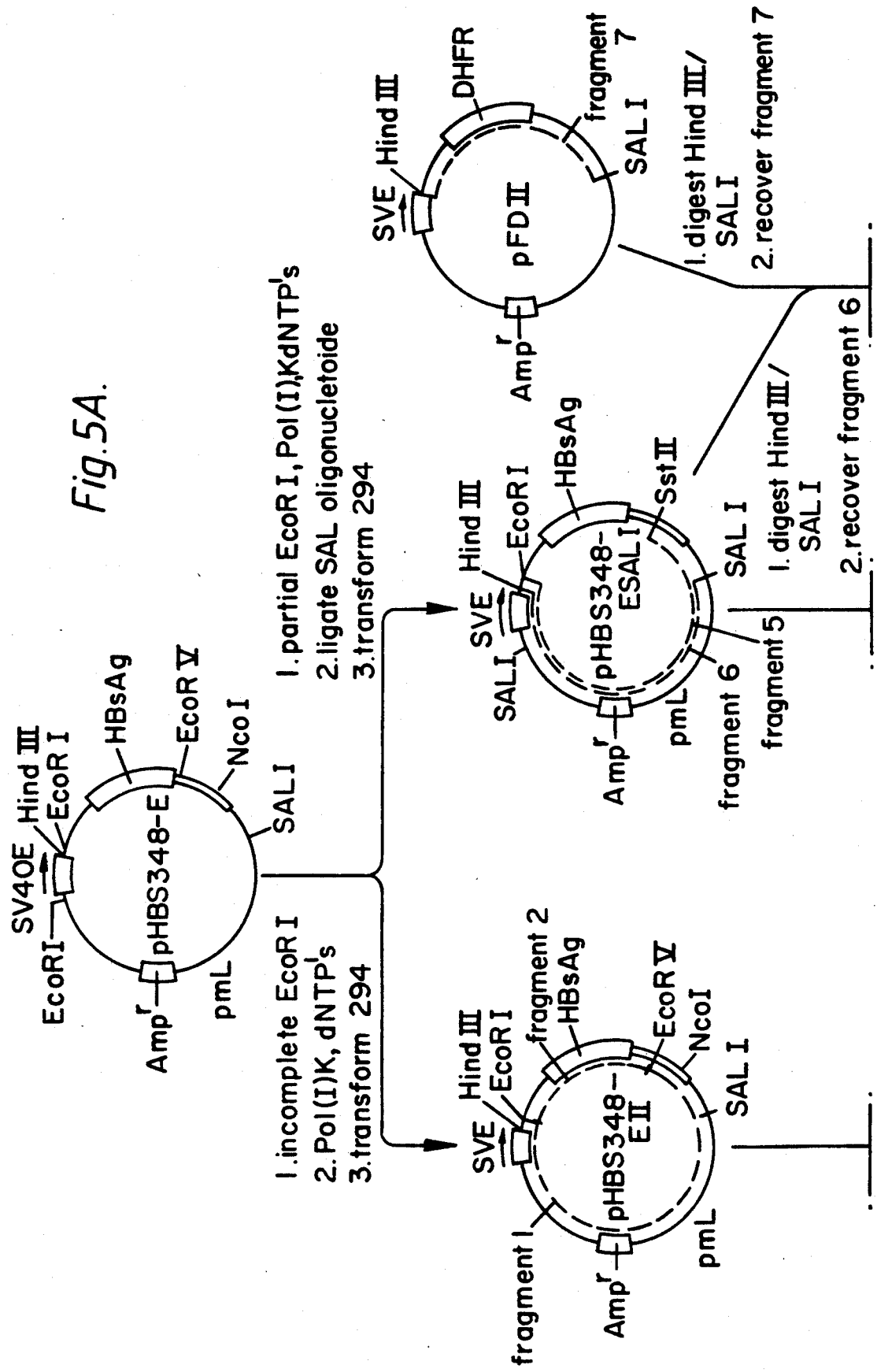
FIGS. 5A-C depicts the construction of a representative recombinant expression plasmid for porcine inhibin.
Figure 5B:
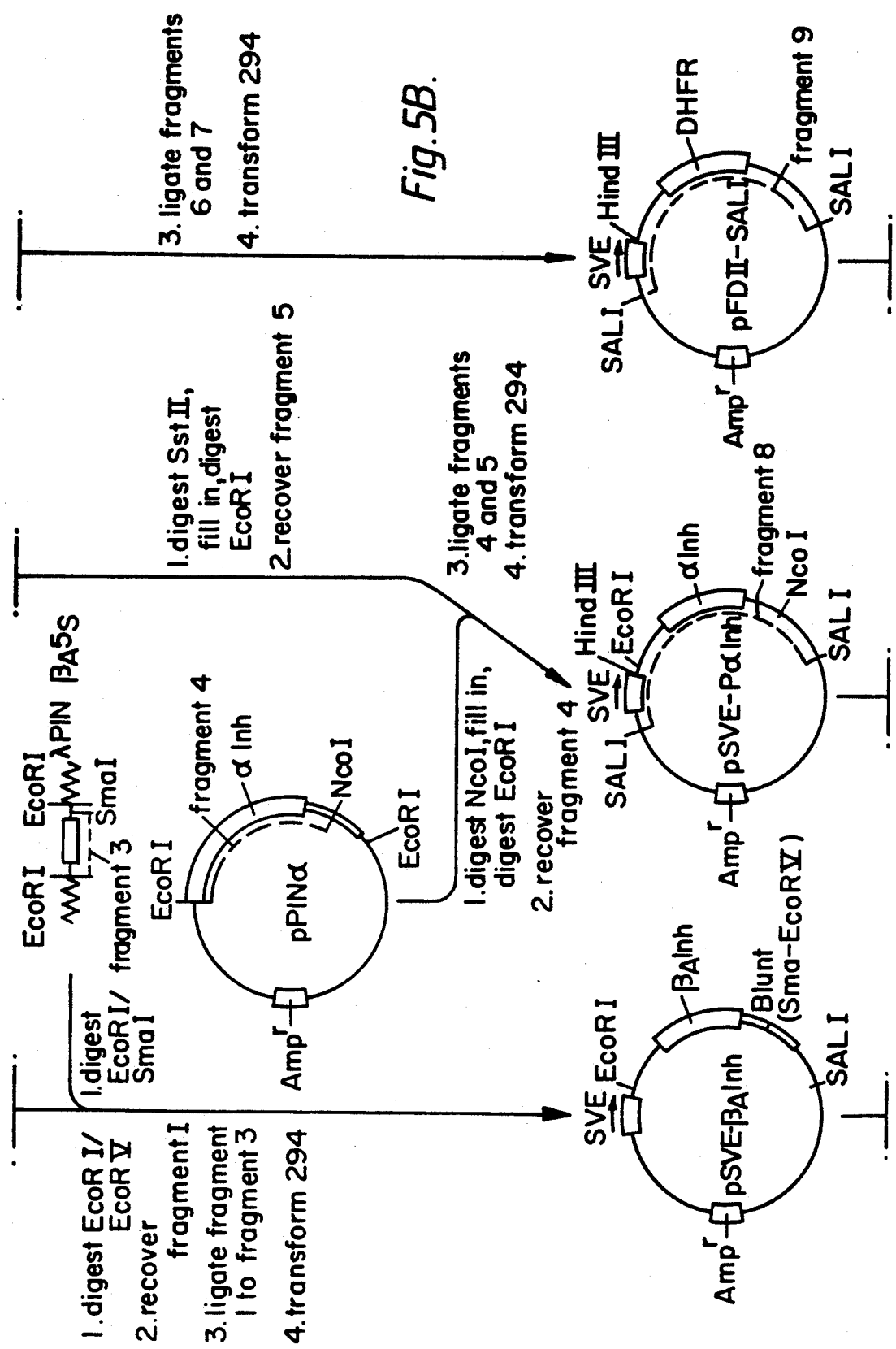
Figure 5C:
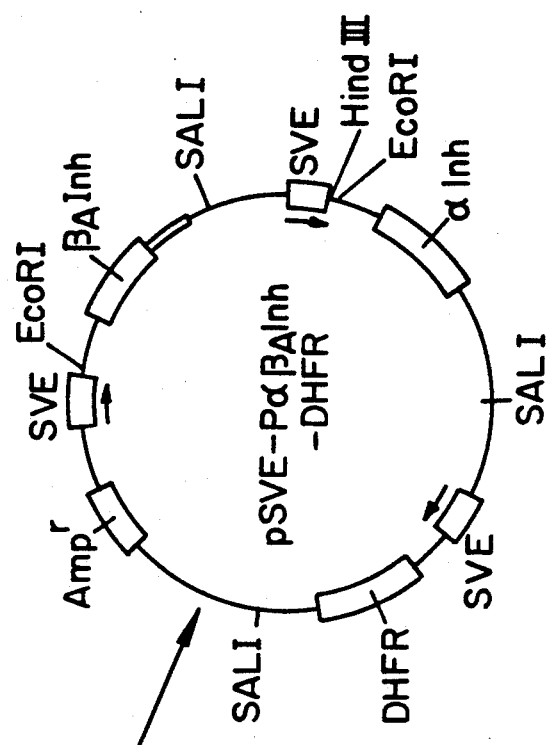

The plasmid used for recombinant synthesis of porcine inhibin was pSVE-PαB$_A$Inh-DHFR. The procedure to construct this plasmid is shown in FIG. 5. This plasmid was constructed as follows:

pHBS348-E (EP 0073656A) was partially digested with EcoRI, blunted with *E. coli* DNA polymerase I (Klenow fragment) and the four dNTPs, ligated and the ligation mixture was transformed into *E. coli* in MM 294 (ATCC 31446). The transformed culture was plated on ampicillin media plates and resistant colonies were selected. Plasmids are screened for the loss of the EcoRI site preceding the SV40 early promoter. A plasmid having the site deleted is referred to as pHBS348-EII.

pHBS348-EII was digested with EcoRI and EcoRI to produce two fragments, fragment I containing the SV40 early promoter, pmI-Amp$^r$ sequences and the HBsAg 3' untranslated region and fragment 2 containing the HBsAg (hepatitis B antigen) coding sequences.

λPINβ$_A$5s containing the coding region for the porcine inhibin $\beta_A$ subunit was digested with EcoRI and SmaI and the 1335 bp fragment (fragment 3) containing the $\beta_A$ coding region recovered by polyacrylamide gel electrophoresis. Fragment I, recovered by agarose gel electrophoresis, was ligated to fragment 3 and the ligation mixture transformed into *E. coli* strain 294 (ATCC 31446). The transformed culture was plated on ampicillin media plates and resistant colonies were selected. Plasmid DNA was prepared from transformants and checked by restriction analysis for the presence of the correct DNA fragments. This plasmid is referred to as pSVE-pβ$_A$Inh.

pHBS348-E (EP 0073656A) was partially digested with EcoRI, blunted with *E. coli* DNA polymerase I (Klenow fragment) and the four dNTPs, and ligated to the synthetic oligonucleotide 5' GGTCGACC-3' containing the SalI recognition site. The transformed culture was plated on ampicillin media plates and resistant colonies were selected. Plasmids were screened for the presence of the extra SalI restriction site. Plasmid DNA is prepared from this construction (pHBS348-ESalI).

λPINα-12s and λPINα-2 were digested with EcoRI and BamHI. A 104 bpEcoRI-BamHI fragment from λPINα-12s containing the 5' coding region and a 1246 bp EcoRI-BamHI fragment from λPINα-2 containing the middle and 3' coding region were recovered and ligated together. The ligation mixture was digested with EcoRI, the enzyme heat denatured, and the mixture ligated to EcoRI-digested pUC9 (BRL). Recombinants were selected and confirmed by restriction analysis. DNA was prepared from the correct plasmid (pPINα).

pPINα, containing the complete coding region for porcine α-inhibin was digested with NcoI and EcoRI, filled in by Pol(I)K in the presence of 4dNTP's, the 1280 bp fragment (fragment 4) was recovered by gel electrophoresis. pHBS348-ESalI was digested with SstII and HindIII, filled in by Pol(I)K in the presence of 4dNTP's, and fragment 5 containing the PML-Amp$^r$ region, SV40 early promoter and HBsAg 3' untranslated region was recovered by gel electrophoresis. Fragments 4 and 5 were ligated together and the ligation mixture was used to transform *E. coli* 294 (ATCC 31446). Recombinants were selected by growing on Ampicillin media plates. The desired recombinant is called pSVE-PαInh.

pHBS348-ESalI was digested with SalI and HindIII and fragment 6 containing the pML-Amp$^r$, and SV40 early promoter was recovered by gel electrophoresis. pFD II (EP 117,060A) was digested with SalI and HindIII and fragment 7 was recovered which contains the normal mouse DHFR gene fused to the HBsAg 3' untranslated region. Fragments 6 and 7 were ligated, and the ligation mixture was transformed into *E. coli* strain 294 (ATCC 31446). The transformed culture was plated on ampicillin media plates and resistant colonies were selected. Plasmid DNA was prepared from transformants and checked by restriction analysis for the presence of the correct DNA fragments. This construction is referred to as pFDII-SalI.

pSVE-PαInh was digested with SalI and fragment 8 was recovered which contains the SV40 early promoter and the α-inhibin coding region fused to the HBsAg 3'-untranslated region. pFDII-SalI was digested with SalI and fragment 9 containing the SV40 early promoter and the mouse DHFR coding region linked to the HBsAg 3'-untranslated region was recovered. pSVE-$\beta_A$Inh was linearized by SalI digestion and ligated to fragments 8 and 9 in a three part ligation. The ligation mixture was transformed into *E. coli* strain 294 (ATCC 31446). The transformed culture was plated on ampicillin media plates and resistant colonies were selected. Transformants were screened for the presence of fragments 8 and 9 in the correct orientation such that transcription from the three SV40 early promoters will proceed in the same direction. This final plasmid is designated pSVE-Pα$\beta_A$Inh-DHFR.

Plasmid pSVE-Pα$\beta_A$Inh-DHFR was transfected into DHFR deficient CHO cells (Urlaub and Chasin, 1980, PNAS 77, 4216–4220). However, any DHFR$^-$ mammalian host cell is suitable for use with this plasmid. Alternatively, any mammalian host cell is useful when the host cell is cotransformed with a plasmid encoding neomycin resistance, and transformants identified by their ability to grow in neomycin-containing medium.

The transfected CHO cells were selected by culturing in 15 HGT$^-$ medium. The cells were allowed to grow to confluency in 15 cm diameter plates. The cells thereafter were cultured in serum free medium for 48 hours prior to harvest. 50 ml of supernatant medium was lyophilized after the addition of 100 mg human serum albumin. The residue was redissolved in 3 ml 1% fetal bovin serum in HDMEM (GIBCO Laboratories, Santa Clara, Calif.), filtered through a Millex-GS 0.22 mM filter (Millipore Corp., Bedford, Mass.) and assayed in duplicate.

The inhibin hormonal activity in the transformant supernatants was determined by an in vitro bioassay using rat anterior pituitary monolayer culture, Vale, W. et al. *Endocrinology*, 91, 562–572 (1972). In brief, 21-day-old female rat anterior pituitaries were collected, enzymatically dispersed and plated in 10% fetal bovine serum in HDMEM (GIBCO Laboratories, Santa Clara, Calif.) into 24-well tissue culture plates (Falcon Plastic, Oxnard, Calif.) on day 1. On day 2, the medium was changed to 1% fetal bovine serum in HDMEM, and the transformant medium sample was added. Incubation was continued for another 48 hours. The monolayer medium was then harvested, and the LH and FSH contents were determined by radio-immunoassay (RIA) using materials provided by The Pituitary Hormone Program of NIADDKD. In this assay, the inhibin-containing CHO cell culture inhibits the basal release of FSH but not LH, as compared to control pituitary cells that received the incubation medium only. The amount of porcine inhibin detected in transformant supernatants was 20 ng/ml and exhibited a dose response curve parallel to that obtained with pure porcine ovarian inhibin.

Immunological cross-reactivity is assayed by a sandwich-type radioimmunoassay. Rabbit antisera are raised against purified porcine follicular inhibin by s.c. immunization of rabbits with the porcine inhibin in Freund's complete adjuvant. The presence of anti-inhibin in the antiserum is detected by incubation of the antiserum with purified porcine inhibin and assaying for the formation of an immune complex by conventional techniques, e.g. gel filtration. An aliquot of the antisera is coated onto goat-anti-rabbit IgG precoated polystyrene test tubes. The recombinant culture supernatant or extract is diluted into phosphate buffered saline and added to the coated tubes, incubated overnight and washed. Another aliquot of the rabbit antiserum is added to the test tubes, incubated and washed. Radioiodinated goat antirabbit IgG is added to the tubes, incubated and unbound goat antiserum removed by washing. The recombinantly produced inhibin cross-reacts with the rabbit antiserum, as evidenced by bound counts on the test tubes which exceed those of controls incubated with culture medium or extracts from untransformed host cells.

EXAMPLE 3

Construction of Human Inhibin Vector and Expression of Human Inhibin in Recombinant Cell Culture-I Expression of human inhibin $\alpha\beta_A$ is facilitated by the discovery that the mature porcine and human $\beta_A$ chains are identical. Thus, construction of a vector for the expression of human inhibin can proceed from plasmid pSVE-$\beta_A$-Inh from Example 1, which contains the porcine $\beta_A$-encoding cDNA.

A λgt 10 library of human ovarian cDNA made from 10 μg of ovarian mRNA was subjected to Southern analysis using radiophosphate labelled porcine cDNA encoding α, $\beta_A$ and $\beta_B$ chains. λHINα-2 was identified as containing coding regions for the human α inhibin chain. The prevalence of hybridizing clones in the case of human α inhibin was considerably less than that found for porcine α inhibin, on the order of 1 in 100,000 human clones hybridized to the 685 bp SmaI fragment of the porcine cDNA for αInh. The β chain clones were also rare, with the $\beta_B$ clones being present at about 3 times the level of $\beta_A$ (1 and 3 out of about 1,000,000 clones, respectively). None of the β chain clones were full length. They were supplemented with a primed cDNA library and assembled generally as described above for the porcine cDNA. The λ inserts were recovered by EcoRl digestion.

Plasmid pHINα-2 is digested with NcoI and SmaI, and the 1049 bp 15 fragment (fragment 10) is recovered by gel electrophoresis. pPinα (Example 2) is digested with EcoRI and PvuII. The 98 bp fragment (fragment 11) is recovered by gel electrophoresis. Fragments 10 and 11 are ligated to adaptor I 5'-CTGCTCCTCTTGCTGTTGGCCCCACG-GAGTGGGCATGGCTGCCAGGGCCC-GGAGCTGGACC-3', in combination with adaptor II which is the complement of adaptor I. The resulting 1208 bp fragment (fragment 12) is treated with Klenow fragment of Pol(I) and the 4 dNTP's and ligated to pHBS348-ESalI which has been restricted with HindIII and SacII and blunt-ended as described in Example 1. Alternatively, pPinα was digested with EcoRI and HpaII, with the fragment encoding upstream from the HpaII site (that is, the first 21 residues of the porcine sequence) being recovered. The adaptor used in this alternative approach was

5'CGGAGCTCGACC3'
3'   CTCGAGCTGG5'.

A plasmid pSVE-HαInh having the correct orientation of fragment 12 is identified by sequence analysis of transformants. This construction (pSVE-HαInh) thus contains the first 24 residues of the porcine signal sequence with the remainder being prepro human inhibin. Plasmid pSVE-HαInh is digested with SalI. The fragment containing the SV40 promoter and human inhibin sequence is ligated to fragment 9 and SalI digested pSVE-$\beta_A$Inh (Example 2). This final plasmid designated pSVE-hα$\beta_A$Inh-DHFR1 is transfected into DHFR-deficient CHO cells and selected as described in Example 2. The culture supernatant contains hormonally active human inhibin.

EXAMPLE 4

Construction of Human Inhibin Vector and Expression of Human Inhibin in Recombinant Cell Culture-II This example is similar to Example 3 except that the pro sequence of human inhibin $\beta_B$ was employed in the place of the porcine $\beta_B$ prepro domain.

The lambda gt10 library of Example 3 yielded λHINα2, as described in example 3, together with λHIN$\beta_A$-5 and -14. The latter two phage were employed to construct the full length $\beta_A$ coding cDNA by ligating the 311 bp EcoR1-HindIII fragment (fragment 13) of λHIN$\beta_A$-5 to the 1101 bp HindIII-HpaI fragment (fragment 14) of λHIN$\beta_A$-14 and ligating this mixture in an EcoR1-SmaI digested mp18 vector (Biolabs). Clones were selected and screened for the appropriate sized insert. An mp18 vector containing the correct insert was treated with DNA polymerase (I) and the four dNTPs in order to render it double stranded, and thereafter digested with XbaI (which cleaves in the mp18 polylinker sequence), blunted with DNA polymerase I and the four dNTPs, and digested with EcoR1. A 1320 bp fragment (fragment 15) was ligated to the EcoR1-EcoRV fragment 1 from Example 2. This ligation mixture was used to transform E. coli 294 cells. Clones were screened by Southern Hybridization and confirmed by restriction analysis. The clone containing the hInh$\beta_A$ coding sequence was designated pSVE-hum$\beta_A$Inh. A plasmid containing the human $\beta_A$ coding sequences and the human α-inhibin sequences together with the DHFR gene is constructed from plasmids pSVE-hum-$\beta_A$Inh, pSVE-HαInh and pFDIISalI as outlined above. Specifically, the SalI fragments from pSVE-HαInh and pFDIISalI which contain the human alpha inhibin and the DHFR genes were ligated with SalI digested pSVE-hum$\beta_A$Inh and a clone containing all three genes was identified. This plasmid, designated pSVE-humα$\beta_A$Inh-DHFR2, was transfected into DHFR−CHO cells and selected by culture in ght− medium. 24 clones were picked, grown to confluency in ght− medium under conditions conventional for CHO cells for two days, allowed to rest for 2 more days and thereafter the culture media were assayed for inhibin and activin activity using the rat pituitary cell assay described above. 4 clones were found to secrete significant levels of human α$\beta_A$ inhibin (hα$\beta_A$-8, 12, 14, and 18). The levels in the culture medium for each clone were, respectively, 125, 125, 200 and 250 ng/ml. Another clone (hα$\beta_A$-11) produced activin as the $\beta_A\beta_A$ homodimer, but no detectable inhibin, as determined by biological activity and the lack of α chain immunoreactivity in the culture medium for this clone. Clone hα$\beta_A$-16 secreted only α chain and was devoid of activin or inhibin activity.

EXAMPLE 5

Recombinant Expression of Human Activin

As reported by Vale et al. (Id.) and Ling et al. (Id.), homodimers and heterodimers of the β chains A and/or B have the opposite effect of inhibin on the pituitary, inducing rather than inhibiting FSH secretion. These proteins, collectively termed activin, are made in α and β chain cotransformants as described in Example 4. However, somewhat less screening for an appropriate transfomant is needed if the initial transfection is conducted with a vector or vectors that do not contain the α chain gene. A suitable vector is readily constructed from the above-described vectors by excising the α chain gene. Plasmid pSVE-hum$\beta_A$Inh from Example 4 is digested with SalI and ligated to fragment 9 (Example 2) containing the DHFR gene. The ligation mixture was used to transfect E. coli 294 cells and colonies selected on the basis of failure to hybridize to the α chain sequence but which did hybridize to the β chain DNA. A clone pSVE-hum$\beta_A$Inh-DHFR was identified from which the α chain DNA had been deleted. This clone is transfected into DHFR−CHO cells as described above. Transformants are identified that secrete activin into the culture medium. Similarly, an expression vector containing a $\beta_B$ coding sequence (reconstituted by ligating DNA encoding the first 34 amino acids of human $\beta_A$ to the remaining coding sequence of the human $\beta_B$ chain)

is readily constructed and cotransfected with pSVE-humβ$_A$Inh-DHFR to produce the heterodimer. The reconstructed human β$_B$ gene also is used in the foregoing plasmids in order to produce αβ$_B$-inhibin which, in the in vitro bioassay, has essentially equivalent biological potency to the αβ$_A$ form of inhibin.

Although the invention has been described with regard to its preferred embodiments, which constitute the best mode presently known to the inventors, it should be understood that various changes and modifications as would be obvious to one having the ordinary skill in the art may be made without departing from the scope of the invention which is set forth in the claims appended hereto.

We claim:

1. A method for producing an inhibin α chain prodomain polypeptide comprising a sequence selected from the group consisting of amino acid residues 1-230 of FIG. 1B, and amino acid residues 1-29 and 30-199 of FIG. 6, comprising (a) constructing a vector that comprises a nucleic acid encoding said prodomain, (b) transforming a host cell with the vector, and (c) culturing the transformed cell under conditions appropriate for expression of said polypeptide.

2. The method of claim 1 wherein the prodomain is a porcine inhibin α chain prodomain fragment consisting of amino acid residues 1-230 of FIG. 1B, or a human inhibin α chain prodomain fragment selected from the sequences consisting of amino acid residues 1-29 and 30-199 of FIG. 6.

3. The method of claim 1 wherein the nucleic acid is operably linked to a promoter recognized by the host cell and comprising further the step of recovering the polypeptide from the culture medium.

4. The method of claim 3 wherein the promoter is a viral promoter.

5. The method of claim 4 wherein the promoter is an SV40 promoter.

6. The method of claim 1 wherein the cell is a cell from a multicellular organism.

7. The method of claim 1 wherein the cell is a prokaryote.

8. Non-chromosomal DNA encoding an inhibin α chain prodomain polypeptide comprising a sequence selected from the group consisting of amino acid residues 1-230 of FIG. 1B, and amino acid residues 1-29 and 30-199 of FIG. 6.

9. The non-chromosomal DNA of claim 8 encoding a porcine inhibin α chain prodomain fragment consisting of amino acid residues 1-230 of FIG. 1B, or a human inhibin α chain prodomain fragment selected from the sequences consisting of amino acid residues 1-29 and 30-199 of FIG. 6.

10. The DNA of claim 8 that is labeled with a detectable moiety.

11. A replicable vector comprising DNA encoding an inhibin α chain prodomain polypeptide comprising a sequence selected from the group consisting of amino acid residues 1-230 of FIG. 1B, and amino acid residues 1-29 and 30-199 of FIG. 6.

12. The vector of claim 11 wherein the prodomain is a porcine inhibin α chain prodomain fragment consisting of amino acid residues 1-230 of FIG. 1B, or a human inhibin α chain prodomain fragment selected from the sequences consisting of amino acid residues 1-29 and 30-199 of FIG. 6.

13. The vector of claim 11 comprising a viral promoter operably linked to the DNA encoding the prodomain polypeptide.

14. A host cell transformed with a replicable vector comprising DNA encoding an inhibin α chain prodomain polypeptide comprising a sequence selected from the group consisting of amino acid residues 1-230 of FIG. 1B, and amino acid residues 1-29 and 30-199 of FIG. 6.

15. The host cell of claim 14 wherein the prodomain is a porcine inhibin α chain prodomain fragment consisting of amino acid residues 1-230 of FIG. 1B, or a human inhibin α chain prodomain fragment selected from the sequences consisting of amino acid residues 1-29 and 30-199 of FIG. 6.

16. The cell of claim 14 that is a eukaryotic cell.

* * * * *